(12) United States Patent
Swartz et al.

(10) Patent No.: US 11,261,216 B2
(45) Date of Patent: Mar. 1, 2022

(54) ENGINEERED HEPATITIS B CORE POLYPEPTIDE

(71) Applicant: The Board of Trustees of the Leland Stanford Junior University, Stanford, CA (US)

(72) Inventors: James R. Swartz, Menlo Park, CA (US); Rinchu Mathew, Palo Alto, CA (US); Marcus John Rohovie, Redwood City, CA (US); Maya Nagasawa, Menlo Park, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 20 days.

(21) Appl. No.: 16/725,626

(22) Filed: Dec. 23, 2019

(65) Prior Publication Data

US 2020/0231632 A1   Jul. 23, 2020

Related U.S. Application Data

(60) Provisional application No. 62/785,866, filed on Dec. 28, 2018.

(51) Int. Cl.
*C07K 14/02* (2006.01)
*C12N 7/00* (2006.01)

(52) U.S. Cl.
CPC ............ *C07K 14/02* (2013.01); *C12N 7/00* (2013.01); *C12N 2730/10122* (2013.01); *C12N 2730/10123* (2013.01)

(58) Field of Classification Search
None
See application file for complete search history.

(56) References Cited

U.S. PATENT DOCUMENTS

| 4,818,527 | A | 4/1989 | Thorton et al. |
| 8,067,011 | B2 | 11/2011 | Davis et al. |
| 2009/0226525 | A1* | 9/2009 | de los Rios ............ B82Y 5/00 424/489 |
| 2013/0156818 | A1* | 6/2013 | de los Rios ............ A61K 31/713 424/400 |
| 2015/0329598 | A1* | 11/2015 | Lu .................... C07K 14/005 530/350 |

OTHER PUBLICATIONS

Winkler, J. Oligonucleotide conjugates for therapeutic applications. Ther. Deliv. (2013) 4(7), 791-809.*
Swartz et al. (2005) "Efficient and scalable method for scaling up cell free protein synthesis in batch mode" Biotechnol. Bioeng. 91, 516-521.
Naismith, et a;. (2008) "An efficient one-step site-directed deletion, insertion, single and multiple-site plasmid mutagenesis protocol" BMC Biotechnology 2008, 8:91.
Wynne et al. (1999) "The Crystal Structure of the Human Hepatitis B Virus Capsid" Mol. Cell, 3, 771-780.
Boyacioglu et al. (2013) "Dimeric DNA Aptamer Complexes for High-capacity-targeted Drug Delivery Using pH-sensitive Covalent Linkages" Mol Therapy Nucleic Acids 2, e107.

* cited by examiner

*Primary Examiner* — Nianxiang Zou
(74) *Attorney, Agent, or Firm* — Pamela J. Sherwood; Bozicevic & Field & Francis LLP

(57) ABSTRACT

Genetically modified HBc polypeptides are provided.

17 Claims, 14 Drawing Sheets

Specification includes a Sequence Listing.

Cargo-loading domain sequence

1. Original His₆ construct:     HHHHHH
2. I₃C-His₆ construct:          IIIC – GS – HHHHHH
3. His₆-I₃C construct:          HHHHHH – GS – IIIC
4. (IG)₂IC-His₆ construct:      IGIGIC – GS – HHHHHH
5. His₆-(IG)₂IC construct:      HHHHHH – GS – IGIGIC

SEQUENCE LISTING

<160> NUMBER OF SEQ ID NOS: 16

<210> SEQ ID NO 1
<211> LENGTH: 149
<212> TYPE: PRT
<213> ORGANISM: Artificial Sequence
<220> FEATURE:
<223> OTHER INFORMATION: Synthetic sequence

<400> SEQUENCE: 1

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr

```
                115                 120                 125
Pro Pro Ala Tyr Arg Pro Pro Asn Ala Pro Ile Leu Ser Thr Leu Pro
        130                 135                 140

Glu Thr Thr Val Val
145

<210> SEQ ID NO 2
<211> LENGTH: 149
<212> TYPE: PRT
<213> ORGANISM: Artificial Sequence
<220> FEATURE:
<223> OTHER INFORMATION: Synthetic sequence

<400> SEQUENCE: 2

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Met Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 3
<211> LENGTH: 149
<212> TYPE: PRT
<213> ORGANISM: Artificial Sequence
<220> FEATURE:
<223> OTHER INFORMATION: Synthetic sequence

<400> SEQUENCE: 3

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Met Gln Asp Gln Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
            100                 105                 110
```

-continued

```
Glu Thr Val Leu Glu Tyr Leu Val Ser Phe Gly Val Trp Ile Cys Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 4
<211> LENGTH: 11
<212> TYPE: PRT
<213> ORGANISM: Artificial Sequence
<220> FEATURE:
<223> OTHER INFORMATION: Synthetic sequence

<400> SEQUENCE: 4

Glu Gly Phe Gly Glu Gly Phe Gly Glu Gly Phe
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic sequence

<400> SEQUENCE: 5

Glu Gly Phe Gly Glu Gly Phe Gly Glu Gly Phe Cys
1               5                   10

<210> SEQ ID NO 6
<211> LENGTH: 5
<212> TYPE: PRT
<213> ORGANISM: Artificial Sequence
<220> FEATURE:
<223> OTHER INFORMATION: Synthetic sequence

<400> SEQUENCE: 6

Ile Gly Ile Gly Cys
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic sequence

<400> SEQUENCE: 7

Ile Gly Ile Gly Ile Cys
1               5

<210> SEQ ID NO 8
<211> LENGTH: 7
<212> TYPE: DNA
<213> ORGANISM: Artificial Sequence
<220> FEATURE:
<223> OTHER INFORMATION: Synthetic sequence

<400> SEQUENCE: 8 gattaca                                                         7

<210> SEQ ID NO 9
<211> LENGTH: 7
<212> TYPE: DNA
<213> ORGANISM: Artificial Sequence
<220> FEATURE:
```

```
<223> OTHER INFORMATION: Synthetic sequence

<400> SEQUENCE: 9 gattaca                                                              7

<210> SEQ ID NO 10
<211> LENGTH: 7
<212> TYPE: DNA
<213> ORGANISM: Artificial Sequence
<220> FEATURE:
<223> OTHER INFORMATION: Synthetic sequence

<400> SEQUENCE: 10 gattaca                                                              7

<210> SEQ ID NO 11
<211> LENGTH: 7
<212> TYPE: DNA
<213> ORGANISM: Artificial Sequence
<220> FEATURE:
<223> OTHER INFORMATION: Synthetic Sequence

<400> SEQUENCE: 11 gattaca                                                              7

<210> SEQ ID NO 12
<211> LENGTH: 7
<212> TYPE: DNA
<213> ORGANISM: Artificial Sequence
<220> FEATURE:
<223> OTHER INFORMATION: Synthetic sequence

<400> SEQUENCE: 12 gattaca                                                              7

<210> SEQ ID NO 13
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 13

Ile Gly Ile Gly Ile Cys
1               5

<210> SEQ ID NO 14
<211> LENGTH: 59
<212> TYPE: DNA
<213> ORGANISM: Artificial Sequence
<220> FEATURE:
<223> OTHER INFORMATION: Synthetic Sequence

<400> SEQUENCE: 14
ggatttgtac tccgccggct taccgttgtc cgtgcgcacc gatcctgagc accctgccg     59

<210> SEQ ID NO 15
<211> LENGTH: 453
<212> TYPE: DNA
<213> ORGANISM: Artificial Sequence
<220> FEATURE:
<223> OTHER INFORMATION: Synthetic Sequence

<400> SEQUENCE: 15
atggatatcg acccgtacaa agaattcggc gcgaccgttg aactgctgtc tttcctgccg     60
```

-continued

```
tctgatttct tcccgtctgt tcgtgacctg ctggacaccg cggcagcact gtaccgtgac    120
gcgctggaat ctccggaaca ttgttctccg catcacactg cgctgcgtca ggcgattctg    180
tgctggggcg acctgatgac cctggcgact tgggttggca ccaacctgga agatccggcg    240
tctcgtgatc tggttgtttc ttacgttaac actaacgttg gtctgaaatt ccgtcagctg    300
ctgtggttcc acatctcttg cctgaccttc ggtcgtgaaa ccgttctgga atacctggtt    360
tcttttggtg tttggattcg tactccgccg gcttaccgtc cgccgaacgc accgatcctg    420
agcaccctgc cggaaaccac tgttgtgtaa taa                                 453

<210> SEQ ID NO 16
<211> LENGTH: 453
<212> TYPE: DNA
<213> ORGANISM: Artificial Sequence
<220> FEATURE:
<223> OTHER INFORMATION: Synthetic Sequence

<400> SEQUENCE: 16
atggatatcg acccgtacaa agaattcggc gcgaccgttg aactgctgtc tttcctgccg     60
tctgatttct tcccgtctgt tcgtgacctg ctggacaccg cggcagcact gtaccgtgac    120
gcgctggaat ctccggaaca ttgttctccg catcacactg cgctgcgtca ggcgattctg    180
tgctggggcg acctgagcac cctggcgact tgggttggca ccaacatgga agatccggcg    240
tctcgtgatc tggttgtttc ttacgttaac actaacgttg gtctgaaatt ccgtcagctg    300
ctgtggttcc acatctcttg cctgaccttc ggtcgtgaaa ccgttctgga atacctggtt    360
tcttttggtg tttggattcg tactccgccg gcttaccgtc cgccgaacgc accgatcctg    420
agcaccctgc cggaaaccac tgttgtgtaa taa                                 453
```

ENGINEERED HEPATITIS B CORE POLYPEPTIDE

BACKGROUND OF THE INVENTION

Virus-like particles (VLPs) are non-infectious, have repetitive surfaces that can display molecules with a high surface density, and have comparable cellular uptake and intracellular trafficking compared to natural virus. All of these functional attributes make them attractive as the assembly core for vaccines, diagnostics, and therapeutics. They can potentially serve as polyvalent scaffolds for the display of nucleic acids, proteins, and other chemical moieties. VLPs are particularly attractive as vaccines as they offer in vivo stability, trafficking to lymph nodes, and stimulation of B and T cell responses by the displayed epitopes. They can also be filled with cargo to serve as delivery vehicles.

Cell-free protein synthesis (CFPS) can be an effective method for producing VLPs, for example those comprising Hepatitis B core protein (HBc), MS2 bacteriophage coat protein, and Qβ bacteriophage coat protein, and the like. CFPS also provides a facile means for introducing non-natural amino acids (nnAAs) into proteins, which allows for the direct protein-protein coupling of antigens to VLPs using Cu(I)-catalyzed [3+2] cycloaddition click chemistry.

Among different types of VLPs, the HBc VLP is a flexible and promising model for knowledge-based display of foreign peptide sequences. The HBc particle was first reported as a promising VLP carrier in 1986. Being one the first VLP candidates and the first icosahedral VLP carrier, HBc VLP has been well characterized and widely used as a carrier for over 100 different foreign sequences. The HBc capsid protein is 183 to 185 amino acids long. The arginine-rich C-terminus of HBc protein is dispensable for VLP assembly, so the HBc protein truncated at amino acid 149 is widely used. The truncated HBc (1-149) proteins can self-assemble into the particle with an average diameter of 30 to 35 nm and a dominant icosahedral symmetry of T=4.

Engineering the core protein and methods of assembly to provide for improved cargo loading is of great interest and is addressed herein.

SUMMARY OF THE INVENTION

Genetically modified hepatitis B core (HBc) proteins are provided, which proteins comprise sequence modification that enhance the stability and/or utility of the protein, including the addition of a cargo-loading domain at the carboxy terminus of the HBc protein. The modifications described herein allow therapeutic cargo, including without limitation RNA, DNA, proteins, small molecules such as chemotherapeutic drugs, and the like, to be loaded into VLPs. The loading may utilize hydrophobic or ion pairing attraction. Optionally the cargo is bound to the interior of the VLP by a disulfide bond.

Methods are provided for producing a cargo-loaded VLP. The cargo is added to a solution containing the HBc protein, e.g. a modified HBc protein disclosed herein, to allow concurrent drug loading and VLP assembly, triggered by an increase in the ionic strength of the solution. After cargo-loaded VLPs are purified and stabilized, they may be further modified by simultaneously attaching molecules that confer different functionalities to the surface, including moieties to enhance serum half-life, e.g. PEG, etc.; specific cell targeting moieties, e.g. proteins including without limitation single chain antibody fragments, aptamers, ligands for cell surface receptors and the like. In some embodiments the targeting moiety targets the VLP to a cancer cell. In some embodiments the targeting moiety targets the VLP to an infected cell, e.g. a pathogen-infected cell.

VLPs comprising the modified HBc proteins described herein can self-assemble in a 0.5 M NaCl solution. In some embodiments, in order to maintain cargo solubility during loading, the VLP assembly is performed in the presence of an organic solvent, for example in the presence of from about 0.5% to about 20%, e.g. at least about 5%, at least about 10% and not more than about 20%, not more than about 15% organic solvent, such as DMSO, DMF, and the like. A non-ionic surfactant may also be included, for example tween-20, etc. at a concentration of from about 0.01% to about 1%, e.g. around 0.1%. After assembly the VLP is treated with a mild oxidizing agent, such as diamine. Following oxidation, disulfide bonds are stable in normal saline and comparable excipients. After the disulfide bonds are reduced, for example upon uptake by a cell, the VLP disassembles in low ionicity solutions. This conditional stabilization allows the release of therapeutic cargo under reducing conditions present in cytoplasm.

In some embodiments, a sequence set forth in SEQ ID NO:1, SEQ ID NO:2 or a comparable HBc polypeptide, is modified by an amino acid substitution at residue A131 to a basic amino acid, e.g. H, K, R, in some embodiments the substitution is A131K. This modification is generally made in combination with a set of amino acid substitutions that reduces the negative charge on the "spike tip" of the protein, i.e. the region of residues 73-81, relative to SEQ ID NO:1 or SEQ ID NO:2. In some embodiments, the set of amino acid changes, relative to SEQ ID NO:1 or SEQ ID NO:2 are I57V, L60S, G63R, D64E, L65V, M66T, T67D, L68F, A69G, T70D, T74N, L76M, E77Q, P79Q, S81A, S87N, T91A, V93I, and F97I. In some embodiments the set of amino acid changes is T74N, L76M, E77Q, P79Q, and S81A. In some embodiments, the amino acid sequence of the HBc protein with a reduced negative charge is SEQ ID NO:3. It has been found that this set of tip substitutions increases the ionic strength required for assembly, e.g. to about 1.5M NaCl. The inclusion of the A131 substitution reduces the ionic strength required for assembly, e.g. less than 1 M, less than 0.75 M, less than 0.5 M, and may be less than 0.25 M.

For loading cargo, the HBc protein may be further modified by addition of a cargo loading domain at the terminus, usually at the C-terminus. The choice of cargo-loading domain may be based on the nature of the intended cargo. Exemplary cargo-loading domains are at least one and usually not more than 15 amino acids in length, for example at least two, at least three, and up to 12, up to 10, up to 8 amino acids in length. In some embodiments a cargo-loading domain comprises one cysteine residue. In some embodiments, where the molecular size of the cargo is less than 2 nm, a cysteine is provided in the cargo-loading domain; and the cargo is selected to have a free sulhydryl, or is modified to introduce a free sulfhydryl.

Exemplary cargo-loading domains include, without limitation, (SEQ ID NO:4) EGFGEGFGEGF; (SEQ ID NO:5) EGFGEGFGEGFC; (SEQ ID NO:6) IGIGC; (SEQ ID NO:7) IGIGIC; RRR; R; IIIC; C; CRC; EEE; etc. Using the methods provided herein, a sequence for a cargo-loading domain can be empirically selected to allow: effective VLP subunit production (accumulation, folding, and purification) and effective subunit assembly into VLPs, while also maximizing number of loaded molecules per VLP and avoiding loss due to proteolysis.

The HBc protein can further comprise one or more unnatural amino acids at a pre-determined site. Unnatural amino acids of interest include without limitation azidohomoalanine, homopropargylglycine, p-acetyl-phenylalanine, p-ethynyl-phenylalanine, p-propargyloxyphenylalanine, p-azido-phenylalanine, etc. The unnatural amino acid(s) may be positioned at the spike of the HBc protein. Sites of interest include, for example, N75, T74, L76, Q77, D78, Q79 and A80. In some embodiments the unnatural amino acid replaces A80. In some embodiments the unnatural amino acid is azidohomoalanine.

HBc polypeptides, or VLP generated therefrom may comprise a conjugated moiety other than an HBc polypeptide, where such a moiety is conjugated to the HBc at the introduced unnatural amino acid, e.g. by click chemistry. Suitable moieties include polypeptides, nucleic acids, polysaccharides, therapeutic drugs, imaging moieties, and the like. In a related embodiment, a method is provided, where the unnatural amino acid in HBc is utilized in a click chemistry reaction to join an additional moiety to the HBc of the invention, or a VLP comprising HBc of the invention.

The HBc polypeptides of this invention can be made by transforming host cells with nucleic acid encoding the polypeptide, culturing the host cell and recovering the polypeptide from the culture, or alternatively by generating a nucleic acid construct encoding the HBc polypeptides and producing the polypeptide by cell free synthesis, which synthesis may include coupled transcription and translation reactions. Also provided are vectors and polynucleotides encoding the HBc polypeptides. In some embodiments a VLP comprising polypeptides of the invention is provided.

In one embodiment of the invention, a method is provided for the cell-free protein synthesis (CFPS) of the protein of the invention. In some embodiments the CFPS product is synthesized; and may further be assembled into a VLP, in a reducing environment. The CFPS product may be contacted with a solution of from about 1M to about 2 M salt, e.g. about 1.5 M salt, e.g. NaCl, etc. The assembled VLP may be isolated in a reducing environment. Following synthesis and assembly into a VLP, the VLP may be switched to an oxidizing environment to generate stabilizing disulfide bonds.

BRIEF DESCRIPTION OF THE DRAWINGS

(FIG. 15A) functionalized with a sulfhydryl and a fluorescent tag (6-FAM) and (FIG. 15B) functionalized with a sulfhydryl, a fluorescent tag, and a hydrophobic loading tag (cholesterol).

DETAILED DESCRIPTION OF THE EMBODIMENTS

Figure 1:
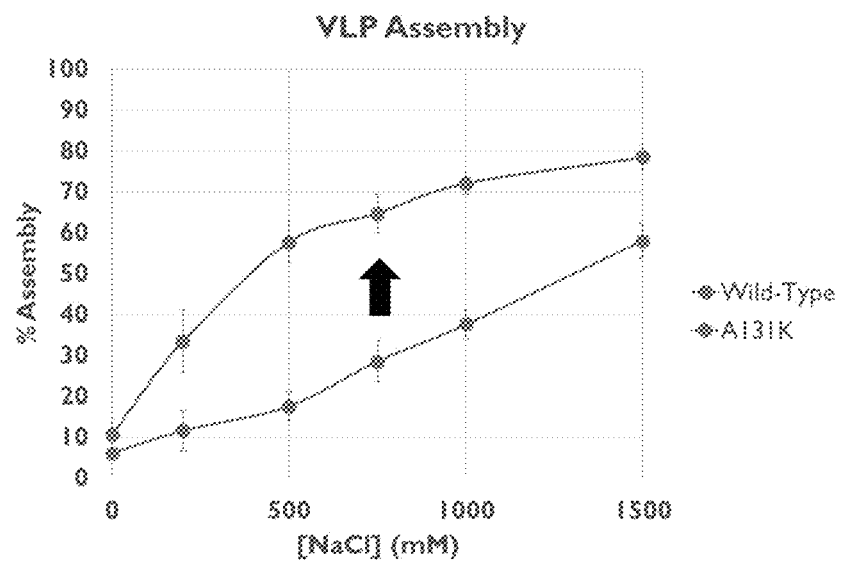
FIG. 1. Successful assembly variant: the A131K mutation in combination with a spike transplant modification allows significant assembly between 500 and 1000 mM NaCl. Error bars represent standard deviation from the mean (n=3) of repeated experiments.

Genetically modified hepatitis B core (HBc) proteins are provided, which proteins comprise sequence modification that enhance the stability and/or utility of the protein, including the addition of a cargo-loading domain at the carboxy terminus of the HBc protein. The modifications described herein allow therapeutic cargo, including without limitation RNA, DNA, proteins, small molecules such as chemotherapeutic drugs, and the like, to be loaded into VLPs. The loading may utilize hydrophobic or ion pairing attraction. Optionally the cargo is bound to the interior of the VLP by a disulfide bond.

The HBc polypeptides of the invention find particular use as a component of a VLP, and particularly a VLP designed for encapsulating cargo. The VLP may additionally be conjugated to one or more additional moieties through, for example, click chemistry. In some embodiments an unnatural amino acid is used to link the HBc protein to the additional moiety(s).

In some embodiments, the invention provides a use of a conjugate, compound, or composition herein in the manufacture of a medicament. In an embodiment, the invention provides a use of a conjugate, compound, or composition herein in the manufacture of a medicament, e.g. a vaccine, for the prevention or treatment of an infection. In some embodiments, the invention provides a use of a conjugate, compound, or composition herein for the prevention or treatment of an infection.

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The term "HBc" refers to the amino acid peptide sequence of the Hepatitis B core protein, or to a truncated version thereof as set forth in SEQ ID NO:1 or SEQ ID NO:2, or a comparable protein, for example a protein modified with one or more disulfide bonds; modified to provide a site for introduction of an non-natural amino acid, comprising tip modifications and the like as set forth in U.S. Pat. No. 9,896,483, herein specifically incorporated by reference.

Various groups may be introduced into the peptide during synthesis or during expression, which allow for linking to other molecules or to a surface. The introduced groups need not be included in the HBc domain itself, but may be introduced as a tag or fusion C-terminal or N-terminal to the HBc domain. Thus cysteines can be used to make thioethers, poly histidines for linking to a metal ion complex, carboxyl groups for forming amides or esters, amino groups for forming amides, and the like. An insertion of 3 amino acids (ASV) after the initiator formyl-methionine to remove a translation initiating non-natural methionine analog by methionyl aminopeptidase may be included to avoid surface conjugation at undesired positions.

In some embodiments an unnatural amino acid is included at one or more defined sites in the protein, including without limitation at residue 80. The HBc polypeptides of the invention may include an unnatural amino acid for the control of direct attachment to a conjugation partner. Conjugation partners may have an active group for conjugation to the unnatural amino acid(s) on the HBc polypeptide. In some embodiments the conjugation partner is modified to comprise an unnatural amino acid, are reacted with a HBc polypeptide, usually a HBc polypeptide that also comprises an unnatural amino acid and that is assembled in a disulfide stabilized VLP. The unnatural amino acid on the conjugation partner is different from, and reactive with, the unnatural amino acid present on the HBc polypeptide(s).

One of skill in the art will understand that minor amino acid changes can be made in the sequence without altering the function of the protein, e.g. changes of 1, 2, 3, 4, 5, 6, 7, 8, 9, or up to about 10 amino acids, and that a full-length protein may be substituted for the truncated versions exemplified herein. HBc is functionally capable of self-assembling to form an icosahedral virus like particle. The HBc polypeptides of the invention comprise amino acid substitutions as described above, which include without limitation, a modification at residue A131, or addition of a cargo-loading domain.

As used herein, the terms "purified" and "isolated" when used in the context of a polypeptide that is substantially free of contaminating materials from the material from which it was obtained, e.g. cellular materials, such as but not limited to cell debris, cell wall materials, membranes, organelles, the bulk of the nucleic acids, carbohydrates, proteins, and/or lipids present in cells. Thus, a polypeptide that is isolated includes preparations of a polypeptide having less than about 30%, 20%, 10%, 5%, 2%, or 1% (by dry weight) of cellular materials and/or contaminating materials. As used herein, the terms "purified" and "isolated" when used in the context of a polypeptide that is chemically synthesized refers to a polypeptide which is substantially free of chemical precursors or other chemicals which are involved in the syntheses of the polypeptide.

The term "polypeptide," "peptide," "oligopeptide," and "protein," are used interchangeably herein, and refer to a polymeric form of amino acids of any length, which can include coded and non-coded amino acids, chemically, or biochemically modified or derivatized amino acids, and polypeptides having modified peptide backbones.

The polypeptides may be isolated and purified in accordance with conventional methods of recombinant synthesis or cell free protein synthesis. Exemplary coding sequences are provided, however one of skill in the art can readily design a suitable coding sequence based on the provided amino acid sequences. Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized. One of skill in the art can readily utilize well-known codon usage tables and synthetic methods to provide a suitable coding sequence for any of the polypeptides of the invention. The nucleic acids may be isolated and obtained in substantial purity. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome. The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art.

As used herein, the term "virus like particle" refers to a stable macromolecular assembly of one or more virus proteins, usually viral coat proteins. The number of separate protein chains in a VLP will usually be at least about 60 proteins, about 80 proteins, at least about 120 proteins, or more, depending on the specific viral geometry. In the methods of the invention, the HBc is maintained in conditions permissive for self-assembly into the capsid structure, particularly reducing conditions. The methods of the invention provide for synthesis of the coat protein in the absence of the virus polynucleotide genome, and thus the capsid may be empty, or contain non-viral components, e.g. mRNA fragments, etc.

A stable VLP maintains the association of proteins in a capsid structure under physiological conditions for extended periods of time, e.g. for at least about 24 hrs, at least about 1 week, at least about 1 month, or more. Once assembled, the VLP can have a stability commensurate with the native virus particle, e.g. upon exposure to pH changes, heat, freezing, ionic changes, etc. Additional components of VLPs, as known in the art, can be included within or disposed on the VLP. VLPs do not contain intact viral nucleic acids, and they are non-infectious. In some embodiments there is sufficient viral surface envelope glycoprotein and/or adjuvant molecules on the surface of the VLP so that when a VLP preparation is formulated into an immunogenic composition and administered to an animal or human, an immune response (cell-mediated or humoral) is raised.

An "effective amount" or a "sufficient amount" of a substance is that amount sufficient to cause a desired biological effect, such as beneficial results, including clinical results, and, as such, an "effective amount" depends upon the context in which it is being applied. In the context of this invention, an example of an effective amount of a vaccine is an amount sufficient to induce an immune response (e.g., antibody production) in an individual. An effective amount can be administered in one or more administrations.

Folding, as used herein, refers to the process of forming the three-dimensional structure of polypeptides and proteins, where interactions between amino acid residues act to stabilize the structure. Non-covalent interactions are important in determining structure, and the effect of membrane contacts with the protein may be important for the correct structure. For naturally occurring proteins and polypeptides or derivatives and variants thereof, the result of proper folding is typically the arrangement that results in optimal biological activity, and can conveniently be monitored by assays for activity, e.g. ligand binding, enzymatic activity, ability to assemble into VLPs, etc.

In some instances, for example where the desired product is of synthetic origin, assays based on biological activity will be less meaningful. The proper folding of such molecules may be determined on the basis of physical properties, energetic considerations, modeling studies, and the like.

Separation procedures of interest include affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural biospecific binding of one molecular species to separate and purify a second species from a mixture. Antibodies are commonly used in affinity chromatography. Preferably a microsphere or matrix is used as the support for affinity chromatography. Such supports are known in the art and are commercially available, and include activated supports that can be combined to the linker molecules. For example, Affi-Gel supports, based on agarose or polyacrylamide are low pressure gels suitable for most laboratory-scale purifications with a peristaltic pump or gravity flow elution. Affi-Prep supports, based on a pressure-stable macroporous polymer, are suitable for preparative and process scale applications.

Proteins may also be separated by ion exchange chromatography, and/or concentrated, filtered, dialyzed, etc., using methods known in the art. The methods of the present invention provide for proteins containing unnatural amino acids that have biological activity comparable to the native protein. One may determine the specific activity of a protein in a composition by determining the level of activity in a functional assay, quantitating the amount of protein present in a non-functional assay, e.g. immunostaining, ELISA, quantitation on coomassie or silver stained gel, etc., and determining the ratio of biologically active protein to total protein. Generally, the specific activity as thus defined will be at least about 5% that of the native protein, usually at least about 10% that of the native protein, and may be about 25%, about 50%, about 90% or greater.

A modified HBc protein of the invention may comprise at least one unnatural amino acid at a pre-determined site, and may comprise or contain 1, 2, 3, 4, 5 or more unnatural amino acids. If present at two or more sites in the polypeptide, the unnatural amino acids can be the same or different. Where the unnatural amino acids are different, an orthogonal tRNA and cognate tRNA synthetase will be present for each unnatural amino acid. In some embodiments a single unnatural amino acid is present at residue 80.

Examples of unnatural amino acids that can be used in the methods of the invention include: an unnatural analogue of a tyrosine amino acid; an unnatural analogue of a glutamine amino acid; an unnatural analogue of a phenylalanine amino acid; an unnatural analogue of a methionine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a n-amino acid; a cyclic amino acid other than proline, etc.

Unnatural amino acids of interest include, without limitation, amino acids that provide a reactant group for CLICK chemistry reactions (see Click Chemistry: Diverse Chemical Function from a Few Good Reactions Hartmuth C. Kolb, M. G. Finn, K. Barry Sharpless Angewandte Chemie International Edition Volume 40, 2001, P. 2004, herein specifically incorporated by reference). For example, the amino acids azidohomoalanine, homopropargylglycine, p-acetyl-L-phenylalanine and p-azido-L-phenylalanine are of interest.

In some embodiments, the unnatural amino acid is introduced by global replacement of methionine on the protein, e.g. methionine can be left out of a cell-free reaction mixture, and substituted by from 0.25-2.5 mM azidohomoalanine (AHA). In such embodiments it is preferred to substitute natural methionines, e.g. M66, with a different amino acid, while an ATG codon is introduced into the coding sequence at the desired site for unnatural amino acid introduction, for example, residue 80.

Alternatively the unnatural amino acid is introduced by orthogonal components. Orthogonal components include a tRNA aminoacylated with an unnatural amino acid, where the orthogonal tRNA base pairs with a codon that is not normally associated with an amino acid, e.g. a stop codon; a 4 bp codon, etc. The reaction mixture may further comprise a tRNA synthetase capable of aminoacylating (with an unnatural amino acid) the cognate orthogonal tRNA. Such components are known in the art, for example as described in U.S. Pat. No. 7,045,337, issued May 16, 2006. The orthogonal tRNA recognizes a selector codon, which may be nonsense codons, such as, stop codons, e.g., amber, ochre, and opal codons; four or more base codons; codons derived from natural or unnatural base pairs and the like. The orthogonal tRNA anticodon loop recognizes the selector codon on the mRNA and incorporates the unnatural amino acid at this site in the polypeptide.

Orthogonal tRNA synthetase can be synthesized exogenously, purified and added to the reaction mix of the invention, usually in a defined quantity, of at least about 10 µg/ml, at least about 20 µg/ml, at least about 30 µg/ml, and not more than about 200 µg/ml. The protein may be synthesized in bacterial or eukaryotic cells and purified, e.g. by affinity chromatography, PAGE, gel exclusion chromatography, reverse phase chromatography, and the like, as known in the art.

The terms "conjugation partner" or "selected additional moiety(s)" are used interchangeably and refer generally to any moiety, for example a peptide or protein, nucleic acid, polysaccharide, label, etc. that is conjugated to a HBc polypeptide of the invention. The conjugation partner may comprise a complementary active group for CLICK chemistry conjugation to the HBc polypeptide of the invention. For example, it may be synthesized with one or more unnatural amino acids, which allow for the conjugation to the unnatural amino acid present on the HBc protein. One of skill in the art will understand that the chemistry for conjugation is well-known and can be readily applied to a variety of groups, e.g. CpG DNA sequences, detectable label, antigen, polypeptide, etc.

In some embodiments the conjugation partner is a structural protein, e.g. a collagen, keratin, actin, myosin, elastin, fibrillin, lamin, etc. In some embodiments the conjugation partner is an immunogen, e.g. a pathogen protein useful in immunization, including without limitation influenza proteins such as hemagglutinin. Virus coat proteins of interest include any of the known virus types, e.g. dsDNA viruses, such as smallpox (variola); vaccinia; herpesviruses including varicella-zoster; HSV1, HSV2, KSVH, CMV, EBV; adenovirus; hepatitis B virus; SV40; T even phages such as T4 phage, T2 phage; lambda phage; etc. Single stranded DNA viruses include phiX-174; adeno-associated virus, etc. Negative-stranded RNA viruses include measles virus; mumps virus; respiratory syncytial virus (RSV); parainfluenza viruses (PIV); metapneumovirus; rabies virus; Ebola virus; influenza virus; etc. Positive-stranded RNA viruses include polioviruses; rhinoviruses; coronaviruses; rubella; yellow fever virus; West Nile virus; dengue fever viruses; equine encephalitis viruses; hepatitis A and hepatitis C viruses; tobacco mosaic virus (TMV); etc. Double-stranded RNA viruses include reovirus; etc. Retroviruses include rous sarcoma virus; lentivirus such as HIV-1 and HIV-2; etc.

Examples of polypeptides and nucleic acids suitable as conjugation partner include, but are not limited to, targeting moieties such as antibodies and fragments thereof, aptamers, etc. In other embodiments a conjugation partner is an antigenic protein such as tumor antigens, viral proteins, bacterial proteins, including tuberculosis antigens, protozoan proteins, including malarial proteins, renin; growth hormones, including human growth hormone; bovine growth hormone; growth hormone releasing factor; parathyroid hormone; thyroid stimulating hormone; lipoproteins; alpha-1-antitrypsin; insulin A-chain; insulin; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES and other chemokines; human macrophage inflammatory protein (MIP-1a); a serum albumin such as human serum albumin; mullerian-inhibiting substance; relaxin A-chain; relaxin B-chain; pro-relaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as αFGF and βFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-18; superoxide dismutase; T-cell receptors; surface membrane proteins; decay accelerating factor; viral antigen such as, for example, a portion of the AIDS envelope; transport proteins; homing receptors; addressins; regulatory proteins; antibodies particularly single chain Fv antibodies; and fragments of any of the above-listed polypeptides.

Cargo. The VLP may encapsulate cargo, e.g. a molecule that will be released when the VLP is inside a cell. Encapsulated cargo is protected within the VLP, and is typically not displayed on the surface of the VLP. Stably loaded cargo is retained within a VLP after washing.

Many molecules are suitable as cargo, including without limitation RNA, e.g. guide RNA, siRNA, antisense RNA and the like; DNA, e.g. double stranded or single stranded DNA, including without limitation plasmids, coding sequences, etc.; proteins such as toxin proteins including, for example, diphtheria A chain, exotoxin A chain, ricin A chain, abrin A chain, curcin, crotin, phenomycin, enomycin, auristatin-E and the like; genetic modifying proteins including without limitation CRISPR; binding proteins such as antibodies or fragments derived therefrom, and the like. Cytotoxic agents are numerous and varied. One exemplary class of cytotoxic agents are chemotherapeutic agents. Exemplary chemotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, duocarmycin, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, mertansine, metoclopramide, mitomycin, mitotane, mitoxantrone, omeprazole, ondansetron, paclitaxel, pilocarpine, prochloroperazine, rituximab, saproin, tamoxifen, taxol, topotecan hydrochloride, trastuzumab, vinblastine, vincristine, vinorelbine tartrate, etc.

In some embodiments a cargo is modified to enhance encapsulation by the VLP, for example by addition of a free sulfhydryl group for conjugation to the HBc protein. Alternatively a cargo agent may be selected that comprises a free sulfhydryl group, such as mertansine. A polar cargo, e.g. a nucleic acid such as ssDNA, RNA, etc., may be conjugated to a hydrophobic group such as, for example, cholesterol to enhance loading. Alternatively one or more polar or charged amino acids can be conjugated to the cargo.

Cell free protein synthesis, as used herein, refers to the cell-free synthesis of polypeptides in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. Such synthetic reaction systems are well-known in the art, and have been described in the literature. The cell free synthesis reaction may be performed as batch, continuous flow, or semi-continuous flow, as known in the art.

The CFPS and other subsequent steps may be performed under reducing conditions, e.g. in the presence of 1 mM DTT or the equivalent. Following assembly of the VLP the conditions may be changed to an oxidizing environment, e.g. by dialysis to remove the reducing agent, optionally in the presence of a salt, e.g. up to about 1M salt, up to about 1.5M salt, up to about 2 M salt, e.g. NaCl, etc., then oxidizing to form disulfide bonds by adding 5-10 mM $H_2O_2$, 5-10 mM diamide, or the equivalent.

In some embodiments of the invention, cell free synthesis is performed in a reaction where oxidative phosphorylation is activated, e.g. the CYTOMIM™ system. The activation of the respiratory chain and oxidative phosphorylation is evidenced by an increase of polypeptide synthesis in the presence of $O_2$. In reactions where oxidative phosphorylation is activated, the overall polypeptide synthesis in presence of $O_2$ is reduced by at least about 40% in the presence of a specific electron transport chain inhibitor, such as HONO, or in the absence of $O_2$. The reaction chemistry may be as described in international patent application WO 2004/016778, herein incorporated by reference.

The CYTOMIM™ environment for synthesis utilizes cell extracts derived from bacterial cells grown in medium containing glucose and phosphate, where the glucose is present initially at a concentration of at least about 0.25% (weight/volume), more usually at least about 1%; and usually not more than about 4%, more usually not more than about 2%. An example of such media is 2YTPG medium, however one of skill in the art will appreciate that many culture media can be adapted for this purpose, as there are many published media suitable for the growth of bacteria such as *E. coli*, using both defined and undefined sources of nutrients (see Sambrook, J., E. F. Fritsch, and T. Maniatis. 1989. Molecular Cloning: A Laboratory Manual, $2^{nd}$ edition. Cold Spring Harbor University Press, Cold Spring Harbor, N.Y. for examples of glucose containing media). Alternatively, the culture may be grown using a protocol in which the glucose is continually fed as required to maintain a high growth rate in either a defined or complex growth medium. The reaction mixture may be supplemented by the inclusion of vesicles, e.g. an inner membrane vesicle solution. Where provided, such vesicles may comprise from about 0 to about 0.5 volumes, usually from about 0.1 to about 0.4 volumes.

In some embodiments, PEG will be present in not more than trace amounts, for example less than 0.1%, and may be less than 0.01%. Reactions that are substantially free of PEG contain sufficiently low levels of PEG that, for example, oxidative phosphorylation is not PEG-inhibited. The molecules spermidine and putrescine may be used in the place of PEG. Spermine or spermidine is present at a concentration of at least about 0.5 mM, usually at least about 1 mM, preferably about 1.5 mM, and not more than about 2.5 mM. Putrescine is present at a concentration of at least about 0.5 mM, preferably at least about 1 mM, preferably about 1.5 mM, and not more than about 2.5 mM. The spermidine and/or putrescine may be present in the initial cell extract or may be separately added.

The concentration of magnesium in the reaction mixture affects the overall synthesis. Often there is magnesium present in the cell extracts, which may then be adjusted with additional magnesium to optimize the concentration. Sources of magnesium salts useful in such methods are known in the art. In one embodiment of the invention, the source of magnesium is magnesium glutamate. A preferred concentration of magnesium is at least about 5 mM, usually at least about 10 mM, and preferably a least about 12 mM; and at a concentration of not more than about 25 mM, usually not more than about 20 mM. Other changes that may enhance synthesis or reduce cost include the omission of HEPES buffer and phosphoenol pyruvate from the reaction mixture.

The system can be run under aerobic and anaerobic conditions. Oxygen may be supplied, particularly for reactions larger than 15 μl, in order to increase synthesis yields. The headspace of the reaction chamber can be filled with oxygen; oxygen may be infused into the reaction mixture; etc. Oxygen can be supplied continuously or the headspace of the reaction chamber can be refilled during the course of protein expression for longer reaction times. Other electron acceptors, such as nitrate, sulfate, or fumarate may also be supplied in conjunction with preparing cell extracts so that the required enzymes are active in the cell extract.

It is not necessary to add exogenous cofactors for activation of oxidative phosphorylation. Compounds such as nicotinamide adenine dinucleotide (NADH), NAD+, or acetyl-coenzyme A may be used to supplement protein synthesis yields but are not required. Addition of oxalic acid, a metabolic inhibitor of phosphoenolpyruvate synthetase (Pps), may be beneficial in increasing protein yields, but is not necessary.

The template for cell-free protein synthesis can be either mRNA or DNA, preferably a combined system continuously generates mRNA from a DNA template with a recognizable promoter. Either an endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Other salts, particularly those that are biologically relevant, such as manganese, may also be added. Potassium is generally present at a concentration of at least about 50 mM, and not more than about 250 mM. Ammonium may be present, usually at a concentration of not more than 200 mM, more usually at a concentration of not more than about 100 mM. Usually, the reaction is maintained in the range of about pH 5-10 and a temperature of about 20°-50° C.; more usually, in the range of about pH 6-9 and a temperature of about 25°-40° C. These ranges may be extended for specific conditions of interest.

Metabolic inhibitors to undesirable enzymatic activity may be added to the reaction mixture. Alternatively, enzymes or factors that are responsible for undesirable activity may be removed directly from the extract or the gene encoding the undesirable enzyme may be inactivated or deleted from the chromosome.

Polypeptides

Polypeptides of the invention comprise an HBc sequence, for example with reference to SEQ ID NO:1 or SEQ ID NO:2, wherein various modifications are made to improve utility, particularly for loading cargo. In some embodiments, a sequence set forth in SEQ ID NO:1, SEQ ID NO:2 or a comparable HBc polypeptide, is modified by an amino acid substitution at residue A131 to a basic amino acid, e.g. H, K, R, in some embodiments the substitution is A131K. This modification is generally made in combination with a set of amino acid substitutions that reduces the negative charge on the "spike tip" of the protein, i.e. the region of residues 73-81, relative to SEQ ID NO:1 or SEQ ID NO:2. In some embodiments, the set of amino acid changes, relative to SEQ ID NO:1 or SEQ ID NO:2 are I57V, L60S, G63R, D64E, L65V, M66T, T67D, L68F, A69G, T70D, I74N, L76M, E77Q, P79Q, S81A, S87N, T91A, V93I, and F97I. In some embodiments the set of amino acid changes is T74N, L76M, E77Q, P79Q, and S81A. In some embodiments, the amino acid sequence of the HBc protein with a reduced negative charge is SEQ ID NO:3. It has been found that this set of tip substitutions increases the ionic strength required for assembly, e.g. to about 1.5M NaCl. The inclusion of the A131 substitution reduces the ionic strength required for assembly, e.g. less than 1 M, less than 0.75 M, less than 0.5 M, and may be less than 0.25 M.

For loading cargo, the HBc protein may be further modified by addition of a cargo loading domain at the terminus, usually at the C-terminus. The choice of cargo-loading domain may be based on the nature of the intended cargo. Exemplary cargo-loading domains are at least one and usually not more than 15 amino acids in length, for example at least two, at least three, and up to 12, up to 10, up to 8 amino acids in length. In some embodiments a cargo-loading domain comprises one cysteine residue. Exemplary cargo-loading domains include, without limitation, (SEQ ID NO:4) EGFGEGFGEGF; (SEQ ID NO:5) EGFGEGFGEGFC; (SEQ ID NO:6) IGIGC; (SEQ ID NO:7) IGIGIC; RRR; R; IIIC; C; CRC; EEE; etc.

The HBc may be modified to provide one or a pair of disulfide bonds, for example relative to SEQ ID NO:1, one or more of the following: SS1: D29C, R127C; SS2: T109C, V120C; SS3: Y132C, N136C; SS4: Y132C, A137C; SS6: R133C, N136C; SS6: R133C, A137C; SS7: P134C, P135C; SSB: P134C, N136C; SS9: P134C, A137C; and SS10: P135C, N136C. In some embodiments the amino acid substitutions are D29C and R127C. In other embodiments the amino acid substitutions are P134C and N136C. In some embodiments the amino acid substitutions are D29C, R127C, P134C and N136C.

The HBc protein can further comprise one or more unnatural amino acids at a pre-determined site. Unnatural amino acids of interest include without limitation azidohomoalanine, homopropargylglycine, p-acetyl-phenylalanine, p-ethynyl-phenylalanine, p-propargyloxyphenylalanine, p-azido-phenylalanine, etc. The unnatural amino acid(s) may be positioned at the spike of the HBc protein. Sites of interest include, for example, N75, T74, L76, Q77, D78, Q79 and A80. In some embodiments the unnatural amino acid replaces A80. In some embodiments the unnatural amino acid is azidohomoalanine.

In some embodiments of the invention, a monomeric form of the HBc polypeptide of the invention is provided. In other embodiments a dimeric form of the HBc polypeptide of the invention is provided. In some embodiments the HBc polypeptide is assembled into a VLP, that can be stabilized by intermolecular disulfide bonds upon oxidation.

Methods of Cargo Loading

The modifications described herein allow therapeutic cargo, including without limitation RNA, DNA, proteins, small molecules such as chemotherapeutic drugs, and the like, to be loaded into VLPs. The loading may utilize hydrophobic or ion pairing attraction. Optionally the cargo is bound to the interior of the VLP by a disulfide bond.

The cargo is added to a solution containing the HBc protein to allow concurrent drug loading and VLP assembly, triggered by an increase in the ionic strength of the solution. After cargo-loaded VLPs are purified and stabilized, they may be further modified by simultaneously attaching molecules that confer different functionalities to the surface, including moieties to enhance serum half-life, e.g. PEG, etc.; specific cell targeting moieties, e.g. proteins including without limitation single chain antibody fragments, aptamers, ligands for cell surface receptors and the like. In some embodiments the targeting moiety targets the VLP to a cancer cell. In some embodiments the targeting moiety targets the VLP to an infected cell, e.g. a pathogen-infected cell. VLPs comprising the modified HBc proteins described herein can self-assemble in a 0.5 M NaCl solution. In some embodiments, in order to maintain cargo solubility during loading, the VLP assembly is performed in the presence of an organic solvent, for example in the presence of from about 0.5% to about 20%, e.g. at least about 5%, at least about 10% and not more than about 20%, not more than about 15% organic solvent, such as DMSO, DMF, and the like. A non-ionic surfactant may also be included, for example tween-20, etc. at a concentration of from about 0.01% to about 1%, e.g. around 0.1%. After assembly the VLP is treated with a mild oxidizing agent, such as diamine. Following oxidation of disulfide bonds are stable in normal saline and comparable excipients. After the disulfide bonds are reduced, for example upon uptake by a cell, the VLP disassembles in low ionicity solutions. This conditional stabilization allows the release of therapeutic cargo under reducing conditions present in cytoplasm.

Methods of Conjugation

Where the active groups for conjugation are reactive azide and alkyne groups, the reaction between HBc and partner may by catalyzed with a copper(I) catalyst at a concentration sufficient for catalysis, e.g. at least about 1 µM, at least about 0.1 mM, at least about 1 mM, etc., as is known in the art. The reaction can be performed using commercial sources of copper(I) such as cuprous bromide or chloride or a compound such as tetrakis(acetonitrile)copper(I)hexafluorophosphate as long as the reaction is performed under anaerobic conditions. The reaction can be run in a variety of solvents, and mixtures of water and a variety of (partially) miscible organic solvents including alcohols, DMSO, DMF, tBuOH and acetone work well. The reaction will proceed at room temperature, and is allowed to proceed to the desired level of completion, e.g. at least about 15 minutes, at least about one hour, at least about 4 hours, at least about 8 hours, or more.

The invention further provides nucleic acids encoding the HBc polypeptides of the invention. As will be appreciated by those in the art, due to the degeneracy of the genetic code, an extremely large number of nucleic acids may be made, all of which encode the HBc polypeptides of the present invention. Thus, having identified a particular amino acid sequence, those skilled in the art could make any number of different nucleic acids, by simply modifying the sequence of one or more codons in a way that does not change the amino acid sequence.

Using the nucleic acids of the present invention that encode a HBc polypeptide, a variety of expression constructs can be made. The expression constructs may be self-replicating extrachromosomal vectors or vectors which integrate into a host genome. Alternatively, for purposes of cell-free expression the construct may include those elements required for transcription and translation of the desired polypeptide, but may not include such elements as an origin of replication, selectable marker, etc. Cell-free constructs may be replicated in vitro, e.g. by PCR, and may comprise terminal sequences optimized for amplification reactions.

Generally, expression constructs include transcriptional and translational regulatory nucleic acid operably linked to the nucleic acid encoding the fusion protein. The term "control sequences" refers to DNA sequences necessary for the expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading phase. Linking is accomplished by ligation or through amplification reactions. Synthetic oligonucleotide adaptors or linkers may be used for linking sequences in accordance with conventional practice.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in in vitro expression systems, such as the T7 promoter.

In addition, the expression construct may comprise additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selection genes are well known in the art and will vary with the host cell used.

Formulations and Uses

The HBc polypeptides, including VLPs comprised of HBc; VLPs comprising cargo, and optionally comprising one or more conjugated moieties, may be provided in a pharmaceutically acceptable excipient, and may be in various formulations. As is well known in the art, a pharmaceutically acceptable excipient is a relatively inert substance that facilitates administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington's Pharmaceutical Sciences 19th Ed. Mack Publishing (1995).

Generally, these compositions are formulated for administration by injection or inhalation, e.g., intraperitoneally, intravenously, subcutaneously, intramuscularly, etc. Accordingly, these compositions are preferably combined with pharmaceutically acceptable vehicles such as saline, Ringer's solution, dextrose solution, and the like. The particular dosage regimen, i.e., dose, timing and repetition, will depend on the particular individual and that individual's medical history.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the reagents, cells, constructs, and methodologies that are described in the publications, and which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

Engineering Hepatitis B Core Virus-Like Particle Assembly

Purification of Hepatitis B core subunits. Historically, HepBc VLPs have been produced and purified as VLPs and not as unassembled monomers or dimers. Obtaining HepBc monomers was not needed for initial applications, and SEC was the simplest method to purify VLPs from most other proteins in the cell-free reactions. After expression of HepBc using either *E. coli* or, in our lab, cell-free protein synthesis (CFPS), the crude mixture was dialyzed against a buffer of increased ionic strength to induce self-assembly of the HepBc VLPs. Then, using a single SEC step, the VLPs were purified based on their large size. Subsequent stabilization and surface attachment were performed and a second SEC step was used to purify the final product. However, this method suffered from two major drawbacks. First, it does not allow purification of HepBc monomers. In order to load our desired cargo, we need to start with high purify HepBc subunits. Others have used VLP assembly of unpurified protein followed by a disassembly reaction to purify subunits, but that method involves treating the VLPs with harsh chemicals (urea, guanidine, etc.) and could reduce yields and product quality after cargo loading and re-assembly. The second drawback is that this method also co-purified large *E. coli* protein complexes.

To remedy these issues, we introduced a hexahistidine tag at the C-terminus of the HepBc monomers to allow purification of the unassembled HepBc monomers using Ni-NTA immobilized metal affinity chromatography (IMAC). Using the hexahistidine tag, we could use relatively harsh imidazole washes to remove most impurities from the CFPS reaction product mixture, which includes other proteins from the crude *E. coli* lysate. Further, once the VLP binds to the targeted cell and is endocytosed, it must escape the endosome to deliver its biomolecular cargo. If it fails to do so and reaches the lysosome, many cargoes will be destroyed. Poly-histidine sequences have been shown previously to allow endosomal escape via the proton sponge effect. The new production process replaces the dialysis and first SEC steps with a buffer exchange step after CFPS to improve binding to the Ni-NTA resin, monomer purification using Ni-NTA, a buffer exchange step to remove the imidazole used to elute the protein from the Ni-NTA resin, and a concentration step to reach the critical concentration needed for VLP assembly (approximately 5 μM).

Although the VLP SEC purifications produced expected SEC profiles, we also verified that our new VLPs were identical using dynamic light scattering (DLS) and transmission electron microscopy (TEM). The DLS data suggests an average diameter of 36.91 nm with a low poly-dispersity index (PDI), implying the particles are of uniform size. The crystal structure analysis suggests a size of approximately 35 nm, which agrees with the DLS analysis. The TEM images also show mostly uniform capsids of the expected size.

We next sought to re-design the binding interface between HepBc dimers to reduce the electric field screening during VLP assembly. To load therapeutic cargo such as nucleic acids via electrostatic interactions, we wanted to reduce the ionic strength required for assembly from the 1.5M NaCl required for the HP spike transplant back to the wild-type level of 0.5M NaCl. The goal was to identify a compensating mutation or mutations that allows assembly at reduced ionic strengths without changing the spike region.

To identify a compensating mutation, we employed a mutagenesis strategy based on rational design. We first searched the literature and used the Robetta ALA Scan web server to identify which residues were important for binding at the "assembly" interface formed when two dimers come together during VLP assembly. We then designed three categories of mutations to: (1) reinforce existing hydrophobic interactions with electrostatic interactions, (2) replace existing hydrophobic interactions with electrostatic interactions, or (3) add new electrostatic interactions where there were no interactions originally. These mutants were produced and tested for assembly at low ionic strengths. A tyrosine at position 132 is the most important residue for VLP assembly. A Y132A mutant is assembly-incompetent. To identify other interfacial residues that encourage VLP assembly we used the Robetta ALA Scan webserver. This server first identifies residues at the binding interface based on proximity. Next, it mutates each residue individually to an alanine in silico. By calculating the ΔΔG(complex), which refers to the change in the change of Gibb's free energy (ΔΔG) upon complex formation, we can determine if the original residue was important or not. If the ΔΔG (complex) is positive, it means the new complex without this residue is less favorable for assembly (a more negative ΔG is more favorable). So the higher the ΔΔG(complex) value, the more important that residue is for binding. Unsurprisingly, Y132 was identified as the most important residue by far. However, a number of other, mostly hydrophobic, residues were also identified.

A rationale design mutant library was generated with single and double mutations that did not change Y132. These residue changes were introduced into the HepBc HP variant with the C-terminal hexahistidine extension. The mutations were chosen based on the aforementioned criteria as well as in silico PyMOL-generated structures based on the Dunbrack backbone-dependent AA Rotamer library. The candidates are listed in Table 1.

TABLE 1

Residue changes evaluated

| Residue 1 | Residue 2 | Backbone-to-Backbone Distance (Å) | Method |
|---|---|---|---|
| S35K | E14 | 8.6 | Reinforce natural attraction |
| A36K | E14 | 6.9 | Reinforce natural attraction |
| A131K | D22 | 8.5 | Reinforce natural attraction |
| P129K | D22 | 7.2 | Reinforce natural attraction |
| P25K | T128D | 5.8 | New partners |
| T33E | V124K | 6.8 | New partners |
| L37E | F18R | 9.3 | Replace existing hydrophobic attraction |

Most variants did not accumulate soluble protein using our CFPS system and most of the remaining did not assemble. It is likely that these mutants folded into alternate structures incapable of assembling into VLPs. Only 1 mutation (A131K) was successful, and allowed assembly with salt concentrations as low as 0.5M NaCl (FIG. 1). This mutation met all of our criteria.

We further studied the A131K mutation that improves HepBc VLP assembly at reduced ionic strengths. The fact that were was only 1 variant that could assemble at all, let alone successfully alter the assembly mechanics, was surprising. We generated an in silico model using Rosetta Remodel. The model suggests that A131K could be involved in two different interactions with the same partners as Y132: (1) a salt bridge with D22, and (2) cation-pi interactions with F23. Previous studies have suggested that cation-pi interactions could be even stronger than salt bridges, particularly when exposed to solvent instead of buried in the hydrophobic core of the protein. These interactions could happen at lower ionic strengths when the hydrophobic contribution of Y132 is not strong enough to initiate self-assembly. Once A131K is attracted to either D22 or F23, Y132 can also interact with them strengthening that interaction and preventing dissociation.

Figure 2:
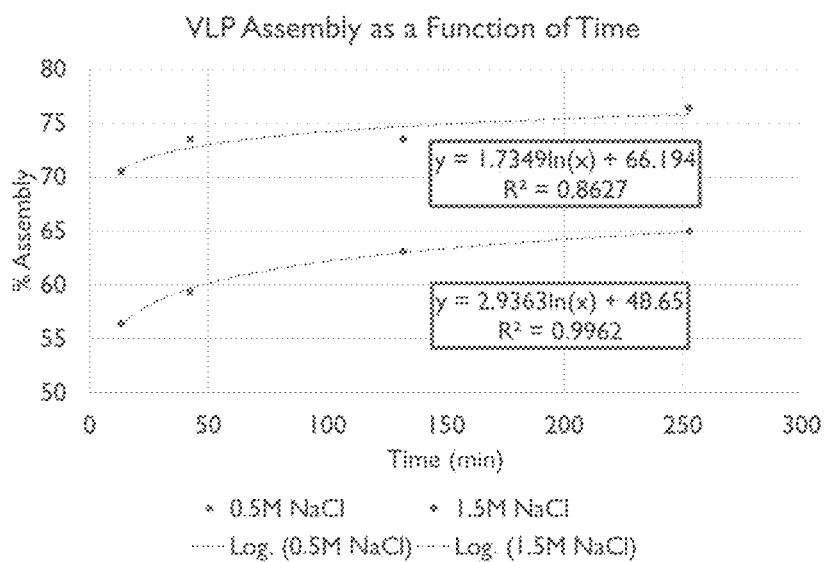
FIG. 2. Assembly kinetics of the A131K HepBc variant.

A study of the assembly kinetics of the A131K variant was performed at both 0.5M and 1.5M NaCl. The results show that although A131K allows assembly at lower ionic strengths, it does not reach the same extent (or rate) of assembly as at higher ionic strengths (FIG. 2).

Figure 3:
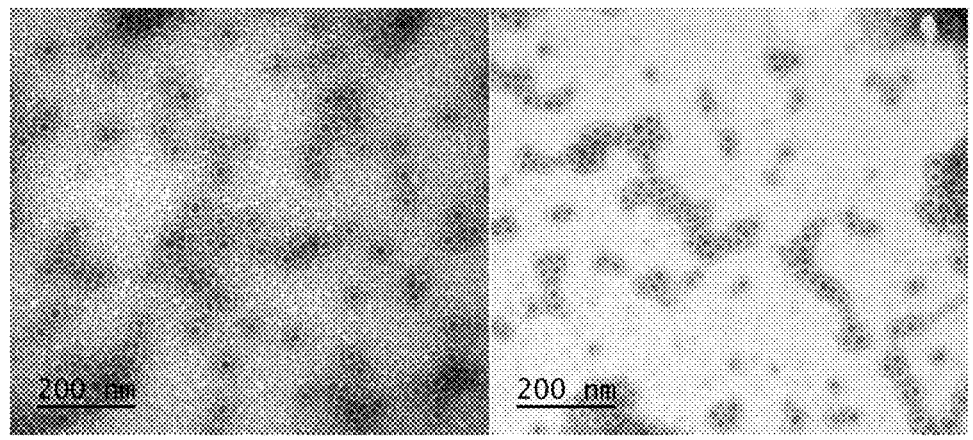
FIG. 3. TEM images of A131K HepBc variant (left) and wild-type HepBc (right) show similar VLP morphology.

Lastly, the A131K variant was analyzed using TEM to show that the mutated VLPs were morphologically similar to the wild-type VLPs. As shown, they appear identical (FIG. 3).

Previous research suggested that the HepBc VLP sequence was highly amenable to mutations. However, the present body of work suggests that this does not apply to the assembly interface. The HepBc monomer can be thought of as having four different domains: (1) the "core" of the protein that defines the fold, (2) the "spike" region that is produced by the alpha helices at the monomer:monomer interface, (3) the "assembly interface" where two dimers bind to begin the self-assembly process, and (4) the C-terminal domain that in the wild-type virus is composed of arginine-rich-repeats to load its viral genome. The "spike" region seems to tolerate mutations both within the homology of the viral family and without. However the "assembly interface" has shown itself to be highly intolerable to changes, especially when reducing hydrophobicity. Although HepBc seems to be highly sensitive to amino acid changes at its assembly interface, one mutation was extremely beneficial. An alanine-to-lysine change at position 131 increased the extent of assembly at 1.5M NaCl and allowed assembly at ionic strengths as low as 0.5M NaCl. Materials and Methods Cell-free protein synthesis reactions. Expression reactions for HepBc proteins used the PANOx-SP cell-free protocol as previously described (Voloshin & Swartz, Biotechnol. Bioeng. 91, 516-521 (2005)). Cell extracts were prepared from A19 met$^+$, ΔtonA, ΔtnaA, ΔspeA, ΔendA, ΔsdaA, ΔsdaB, ΔgshA E. coli cells (strain KC6) grown in a Braun 10 L Biostat C fermenter. In addition to this extract, the small molecule reagents necessary for protein synthesis, purified T7 RNA polymerase, and the plasmid of interest were added. The plasmid was prepared using Qiagen Maxiprep purification kits and included an isopropanol/ethanol wash step. In addition to the standard amino acids, we also added 5 µM of $^{14}$C-leucine to enable quantification of the synthesized protein by measuring incorporated radioactivity. The reactions were performed at multiple scales: 50 µL in 2 mL Eppendorf tubes, 600 µL in covered 6-well tissue culture plates, or 6 mL in covered 10 cm petri dishes. The reactions were incubated at 20-30° C. for various times. Protein concentrations were determined by measuring the incorporated radioactivity using liquid scintillation counting. Total proteins samples were measured directly and soluble protein samples were measured after removing insolubles with centrifugation at 10 k×g for 15 min. Both samples are precipitated on Whatman filter paper with 5% trichloroacetic acid before being washed three times with 5% trichloroacetic acid to remove unincorporated $^{14}$C-leucine.

Original VLP purification method. HepBc proteins were expressed using standard cell-free protein synthesis reactions as described above. The initial purification strategy dialyzed the reactions against 50 mM Tris, pH 7.4 with 0.5-1.5M NaCl for 4 hr and again for 16 hr to induce VLP assembly in the cell-free protein synthesis reactions. Assembled VLPs were quantified and purified by applying 200 µL of the samples to a 2.2 mL Sepharose 6 Fast Flow size-exclusion chromatographic column and eluting with the assembly buffer. Twenty-four 150 µfractions were collected. The HepBc concentration in each fraction was determined by measuring the radioactivity using liquid scintillation counting. The first peak (typically between fractions 5 and 10) was collected as the VLPs. These VLPs were subsequently oxidized using 20-50 mM diamide to form the stabilizing disulfide bonds. The diamide was then removed by dialyzing the samples against 50 mM Tris, pH 7.4 for 4 hr and again for 16 hr.

Improved VLP purification method. HepBc proteins were expressed using standard cell-free protein synthesis reactions as described above. The improved purification strategy first used Sephadex G25 columns to exchange the samples into a 50 mM Tris, 25 mM Imidazole, 0.1% Tween-20, pH 7.4 buffer solution. Insolubles were removed using centrifugation at 10 k×g for 15 min before loading the soluble fraction onto the Ni-NTA column. After loading, the Ni-NTA column was washed with 4 column volumes (CV) of 50 mM Tris, 25 mM Imidazole, 0.1% Tween-20, pH 7.4 and then eluted with 50 mM Tris, 250 mM Imidazole, 0.1% Tween-20, pH 7.4 (5CV total). Fractions with HepBc protein were then applied to SEC columns containing Sephadex G25 resin (2.5 mL of sample loaded on 8.3 mL of resin) to remove imidazole and exchange them into 50 mM Tris, 0.1% Tween-20, pH 7.4. Samples were concentrated using stirred cell concentrators or ultrafiltration-based centrifugal concentrators using 3 kDa molecular weight cutoff filters from Millipore. VLP assembly was induced at 0.5-1.5M NaCl by adding a stock solution of 50 mM Tris, 5M NaCl, 0.1% Tween-20, pH 7.4. Assembled VLPs were quantified and purified by applying 200 µL of the samples to 2.2 mL Sepharose 6 Fast Flow size-exclusion chromatographic resin, eluting 24×150 µL fractions. Protein concentration in each fraction was determined by measuring the radioactivity using liquid scintillation counting. The first peak (typically between fractions 5 and 10) was collected as the VLPs. These VLPs were subsequently oxidized using 20-50 mM diamide. The diamide was then removed by using Sephadex G25 resin to exchange the samples into 50 mM Tris, 0.1% Tween-20, pH 7.4.

Further VLP analysis using dynamic light scattering and transmission electron microscopy. After purifying the VLPs as described above, dynamic light scattering and transmission electron microscopy were used to verify that the VLPs were actually intact capsids of the appropriate diameter. Particle size distribution was determined using a Malvern Zetasizer ZS instrument. For particle size, a 50 µL sample was placed into an ultra-micro cuvette (8.5 mm window height, BrandTech) and analyzed for mean particle diameter using dynamic light scattering. Data was analyzed using Zetasizer software v6.12. For particle morphology, a 5 µL sample was applied to 300-mesh Formvar/carbon coated copper grids (Electron Microscopy Sciences) and negatively stained with 1% uranyl acetate. TEM images were obtained using a JEOL JEM-1400 120 kV electron microscope equipped with a Gatan Orius CCD camera.

Assembly mutagenesis study. The HepBc mutant library for altering the VLP assembly was divided into two parts. The first part contained single and double mutants that added new electrostatic pairs (arginine/lysine plus aspartate/glutamate). This method attempted to reduce the ionic strength required for assembly without drastically altering the assembly mechanism, predicted to be based on hydrophobicity. The second part removed all hydrophobicity from the interface before adding new electrostatic pairs. This method attempted to drastically alter the assembly mechanism to reduce its reliance on hydrophobicity, thereby lowing the ionic strength required for assembly. All mutants in the second part contained the Y132A mutation. All variants were produced using QuikChange mutagenesis and primers from IDT (Liu & Naismith, BMC Biotechnol. 8, 91 (2008)). The sequences were verified through DNA sequencing by Sequetech.

Kinetics of assembly study. To determine the kinetics of VLP assembly, VLPs were analyzed for assembly immediately after increasing the ionic strength at a series of time points. Assembly was determined as described above. Briefly, 200 µL of the samples was applied to pre-equilibrated 2.2 mL Sepharose 6 Fast Flow size-exclusion chromatographic columns, collecting 24×150 L fractions in 50 mM Tris, 0.5 or 1.5M NaCl, 0.1% Tween-20, pH 7.4. The HepBc concentration in each fraction was determined by measuring the radioactivity using liquid scintillation counting. The first peak (typically between fractions 5 and 10) was determined to be the VLPs. Although the use of chromatography to determine kinetics is not ideal as it takes some time for the sample to pass through the resin, mean times used for the kinetics calculations were the elution times of the peak fractions associated with the VLP to minimize bias.

Example 2

Loading and Retention of Cargoes with Relatively Small Molecular Weights

The targeted delivery of active molecules specifically to intended cells within a complex organism was envisioned more than 100 years ago, but has yet to be effectively achieved. For example, efficient targeted delivery of anti-cancer drugs has the potential to improve drug efficacy at the tumor site and to reduce side effects. For this purpose, antibody-drug conjugates (ADCs) have been intensively studied and developed. However, they suffer from several limitations including structural heterogeneity, instability, toxicities, and limited solubility. In contrast, nanoparticle (NP)-based delivery agents, including liposomal, polymer-based, metal-based, and protein-based NPs, have the potential to provide safer and more effective delivery by encapsulating anti-cancer drugs inside the particle with a much higher cargo/carrier ratio.

Among different types of NPs, engineered Hepatitis B core (HepBc) virus-like particles (VLPs) provide desirable characteristics. However, to be useful for the delivery of agents such as anti-cancer drugs, the VLPs must be loaded with many, preferably hundreds, of molecules of the agent. Further, the molecules must be retained inside of the VLP until the VLP enters the target cell. This example describes modified VLPs and methods to satisfy these needs.

Wynne et al. (Mol. Cell, 3, 771 (1999)) describe the structure of the HepBc capsid (VLP) indicating that the C-terminal region of the HepBc monomer comprises the inner surface of the VLP. They further show that the capsid shell has multiple pores of different sizes with the largest pore dimension being about 21 Å.

Figure 4:
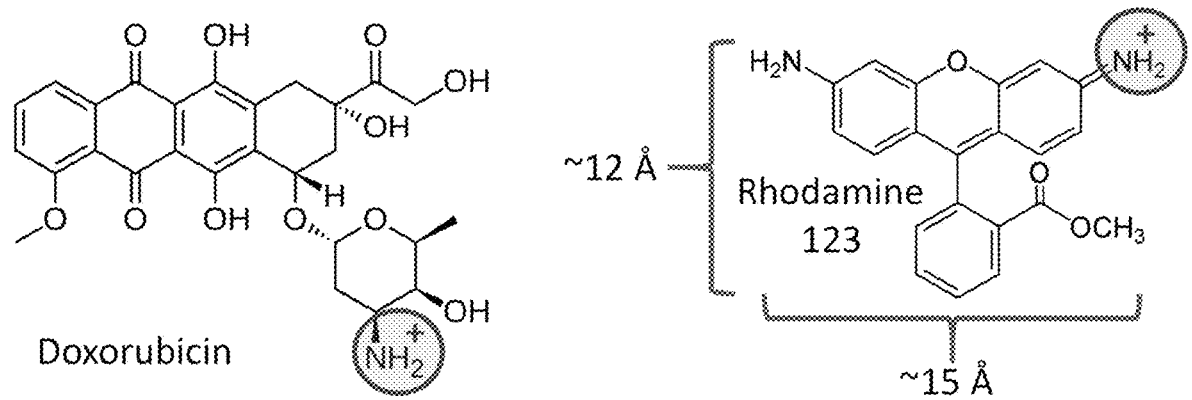
FIG. 4. Size estimations for doxorubicin and Rhodamine 123 indicate that they are small enough to pass through the largest of the VLP pores for which the largest dimension is about 21 Å.

Here, a cargo-loading domain was introduced on the C-terminus, which defines the internal surface of the VLPs once assembled, to expand the HepBc VLP's capabilities to load and retain small molecules inside. The first loading domain was designed to take advantage of hydrophobic and electrostatic attractions to load anti-cancer drugs such as doxorubicin. FIG. 4 shows the molecular conformation of doxorubicin with hydrophobic and positively charged features. To facilitate development of effective VLP designs and loading protocols, a fluorogenic surrogate, Rhodamine 123, was used as it also offers hydrophobic and positively charged features while enabling convenient measurement of loading efficiency. The HepBc C-terminal loading domain shown at the top of FIG. 5 was designed to provide hydrophobic and ion pairing attractive forces for the adsorption of such cargo. The inclusion of phenylalanine residues provides pi-stacking hydrophobic attractions to the drug's ring structures and the negatively-charged glutamate residues provides ion pairing attractions to the drug's positively-charged amine group. Glycine residues are provided between those amino acids so the hydrophobic and negatively charges side chains are facing in the same direction for better interaction with the drugs.

Figure 5:
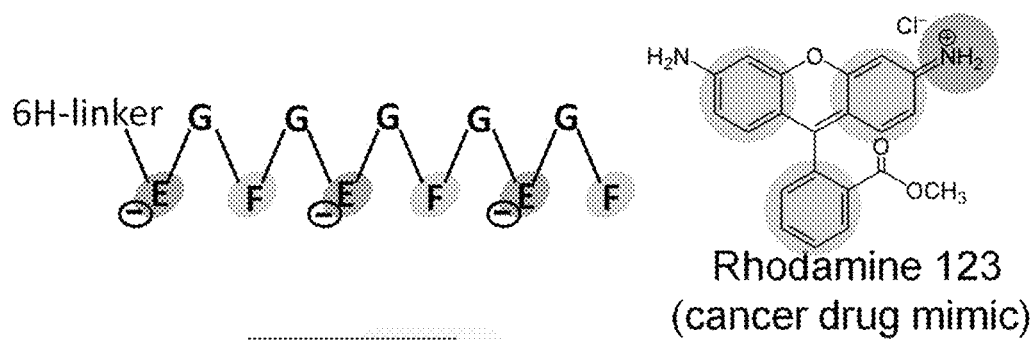
FIG. 5. Results from initial loading experiment. The HepBc C-terminal loading domain is shown in the upper left corner and has both hydrophobic and negatively charged residues to attract the hydrophobic and positively charged cancer drug mimic, Rhodamine 123. The SEC chromatogram shows good VLP assembly efficiency and the suggested loading of about 1000 molecules of the cargo per VLP.
Figure 5:
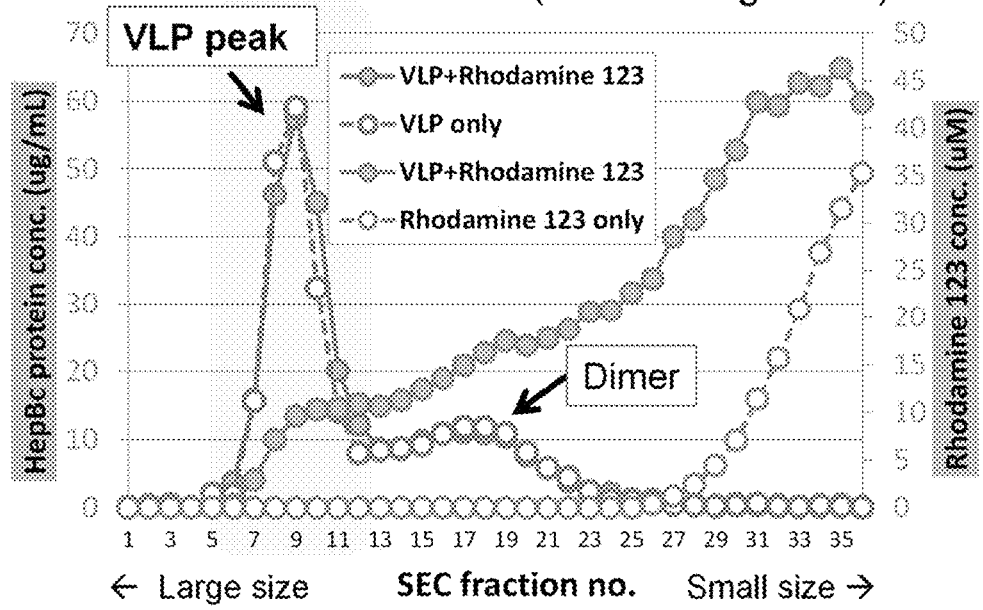
Figure 6:
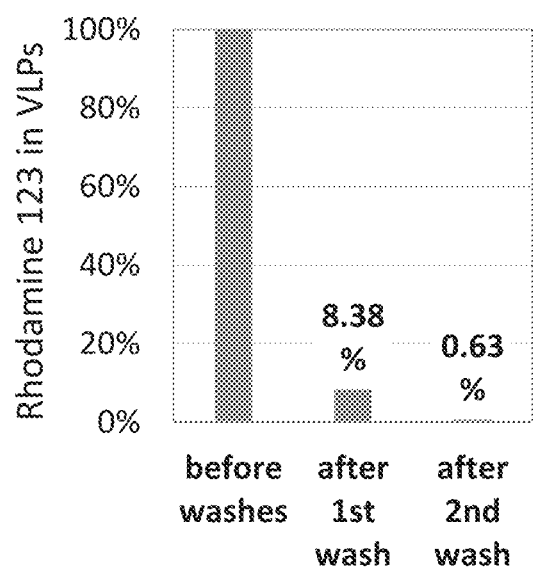
FIG. 6. Successive SEC column washes of the Rhodamine 123 loaded VLPs indicates that the cargo leaks out of the pores in the VLP shell.

The addition of this new oligopeptide after the hexahistidine purification tag was shown to allow HepBc subunit folding during CFPS and to also allow VLP assembly. After this HepBc subunit derivative was purified by Ni-NTA chromatography, the subunit preparation was mixed with Rhodamine 123 and assembly was stimulated by adding a concentrated NaCl solution to increase the ionic strength. The chromatogram in FIG. 5 shows that the presence of the Rhodamine 123 did not prevent VLP assembly. In addition, a significant fraction of the added Rhodamine 123 became associated with the VLP, about 1000 molecules per VLP. However, FIG. 6 indicates that the loaded cargo was lost during the wash steps implemented to remove any Rhodamine 123 that might have been loosely adsorbed to the outer VLP surface. As mentioned the VLP shell has pores with dimensions up to 21 Å and as indicated in FIG. 4, the smallest dimension of the Rhodamine 123 molecule is about 12 Å. This analysis suggests that the loaded fluorophore leaked out through the pores.

Figure 7:
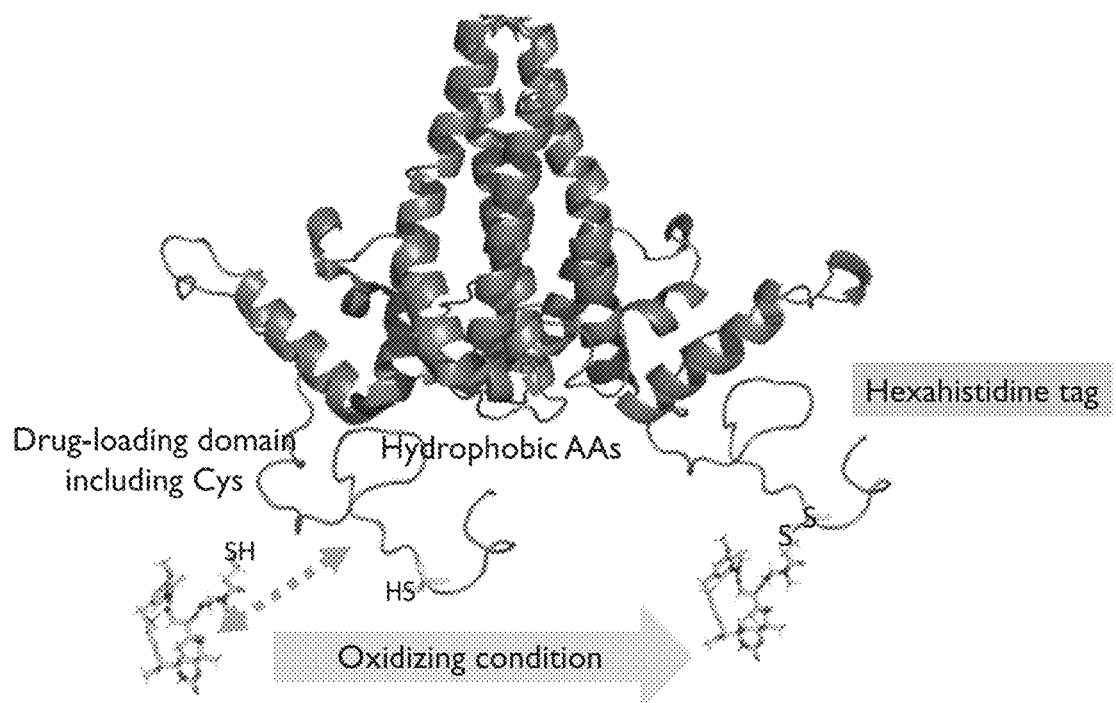
FIG. 7. Schematic of HepBc dimer subunit with a C-terminal cargo-loading domain that also contains a cysteine residue for disulfide bond retention of cargo molecules displaying a sulfhydral moiety. In this case, the loading domain comprises hydrophobic residues to attract hydrophobic cargo molecules. The hexahistidine extension used for subunit purification and triggering of endosomal escape is also shown.

To solve this leakage problem, the loading domain was re-designed to supplement a hydrophobic attraction for loading with a covalent linkage for retention. A disulfide bond linkage is preferred since it provides excellent stability during product purification, formulation, storage, and administration; but it will be dissociated to release the cargo within the reducing environment of the targeted cell interior. This new protein design is illustrated in FIG. 7. Mertansine was selected as a model anti-cancer drug because it includes a sulfhydryl group that can form disulfide bonds. Mertansine is one of the most commonly used tubulin polymerization inhibitors for ADC because of its highly potent cytotoxicity, and is also used for the clinically approved ADC, Kadcyla. Again, a fluorogenic mimic was used for VLP development to facilitate testing of the modified HepBc subunits and the concurrent loading and assembly protocol. The molecular structures of Mertansine and, the fluorogenic mimic (BODIPY FL-Cysteine (BDFL)) are shown in FIG. 8.

Figure 9:
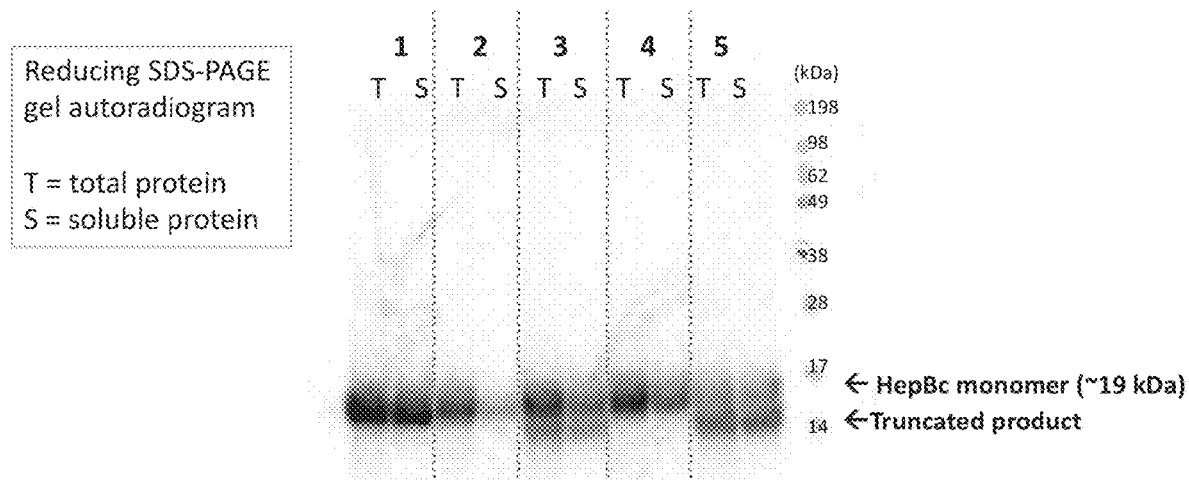
FIG. 9. Reducing SDS-PAGE gel autoradiogram of HepBc mutants with different C-terminal cargo-loading sequences. Shown are cargo loading domain sequences SEQ ID NO: 8, SEQ ID NO:9, SEQ ID NO:10. SEQ ID NO:11, SEQ ID NO:12.
Figure 10:
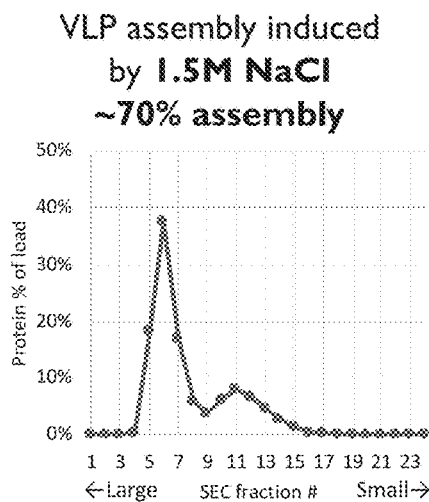
FIG. 10. Improving VLP assembly (for HepBc subunits with HP spikes) by increasing sodium chloride concentration for stronger hydrophobic interactions.
Figure 10:
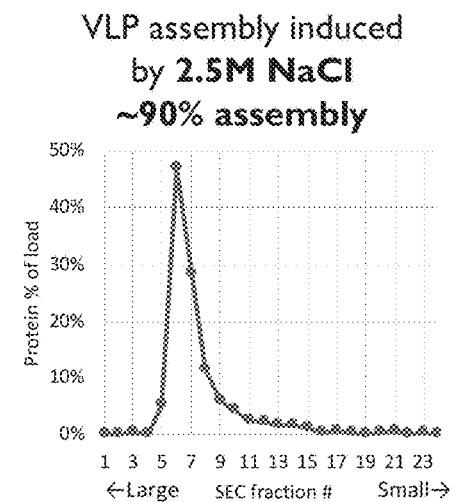

FIG. 9 indicates another required characteristic of these new C-terminal loading domains. In addition to avoiding interference with subunit protein folding and with VLP assembly, the C-terminal extensions must be selected for molecular stability. The addition of $^{14}$C-leucine to the CFPS reaction allows visualization of the HepBc protein products that accumulate during HepBc subunit production. The autoradiogram indicates that, surprisingly, C-terminal extensions with the hexahistine purification tag N-terminal to the loading domain are not stable, presumably due to proteolytic cleavage. However, using the opposite order allows only the desired, intact HepBc derivative to accumulate. Since adsorptive cargo loading is now only mediated by hydrophobic attractions, VLP assembly at higher ionic strengths (to increase attractive forces between the C-terminal loading domain and the hydrophobic cargo) was tested. FIG. 10 indicates that better VLP assembly is achieved using 2.5 M NaCl rather than 1.5 M NaCl.

Figure 8:
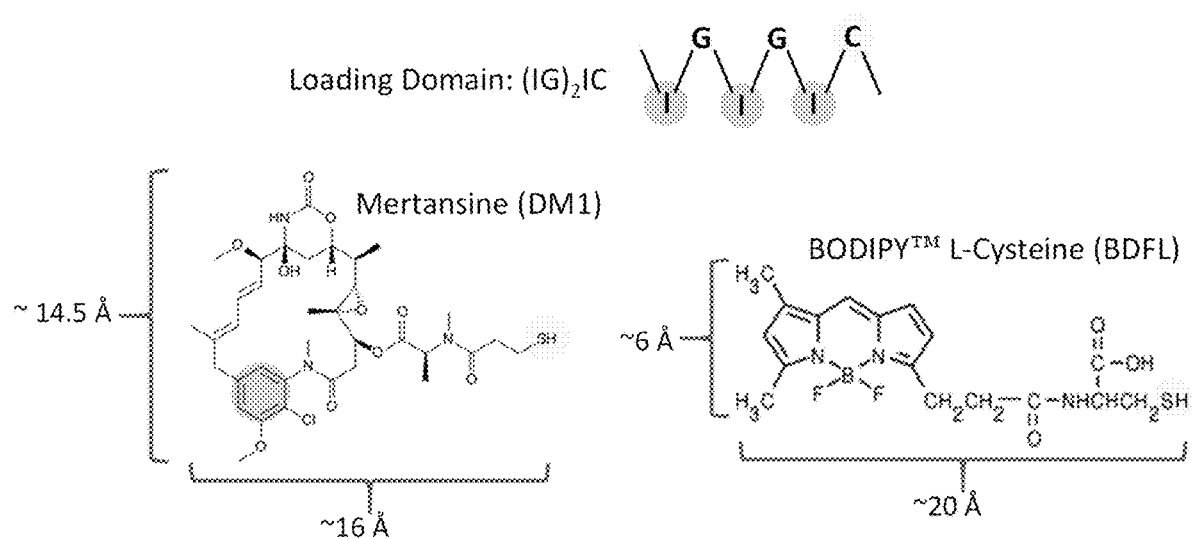
FIG. 8. Schematic of HepBc C-terminal loading domain for hydrophobic cargo and disulfide retention. Two example cargoes, Mertansine (DM1) and BDFL, and their dimensions are shown.
Figure 11:
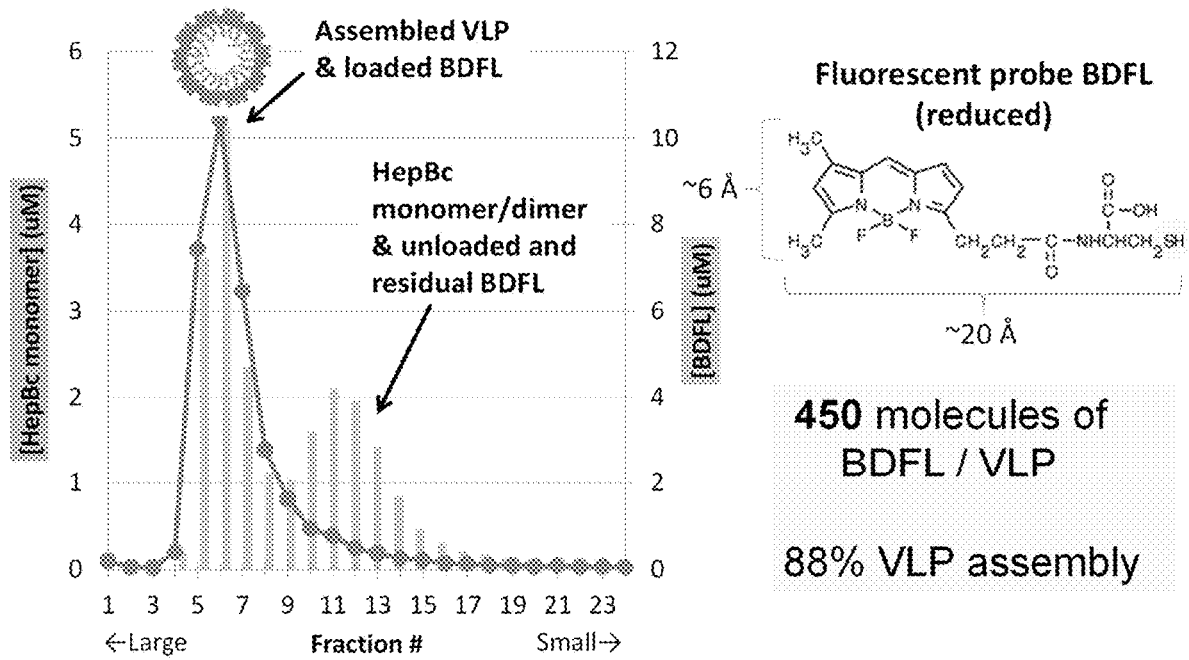
FIG. 11. Size-exclusion chromatogram showing loading & conjugating a small molecule dye (Bodipy FL-Cysteine, BDFL) via cysteines. The BDFL-loaded (and conjugated) VLPs were subjected to significant washing prior to this analysis, proving that the BDFL associated with the VLP is conjugated.

Using the newly designed loading domain shown at the top of FIG. 8, ~450 molecules of BDFL were loaded and retained per VLP after several washes as indicated by FIG. 11. First the BDFL and purified HepBc subunits were mixed together, and assembly was triggered by adding a concentrated NaCl solution. Next, disulfide bonds were formed both to stabilize the assembled VLP and to tether the cargo to the loading domain by incubating with 10 mM diamide, a mild oxidizing agent. SEC buffer exchange steps were then used to remove the diamide as well as unloaded and untethered cargo.

Figure 12:
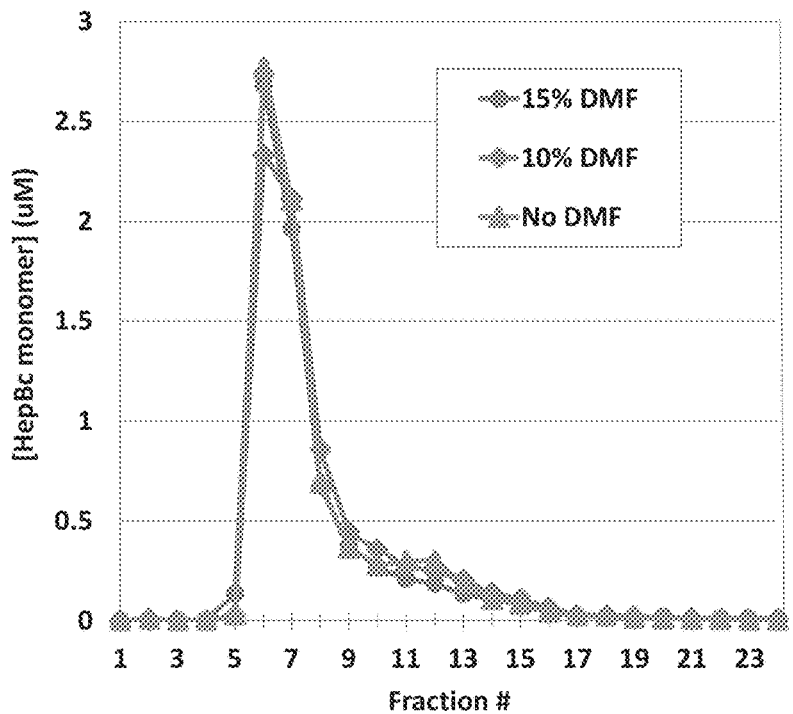
FIG. 12. SEC chromatograms showing excellent VLP assembly in solutions containing DMF (dimethyl formamide).

Initial attempts to load Mertansine encountered a severe problem. Increasing the ionic strength to trigger VLP assembly caused the Mertansine to rapidly precipitate, preventing significant loading of Mertansine inside of the VLPs. Surprisingly, VLP assembly was still efficient even when 10% and 15% of the solvent, dimethyl formamide (DMF) was included in the assembly solution (FIG. 12). The same was true in 15% dimethyl sulf oxide (DMSO), a pharmaceutically acceptable solvent. Both solvents avoided Mertansine precipitation when VLP assembly was triggered by increasing the ionic strength with the addition of 2.5 M NaCl. The loaded VLPs were washed using SEC chromatography. The amount of loaded Mertansine was determined to be >300 molecules per VLP after reducing the disulfide bonds, disassembling the VLPs with 2% SDS and measuring the released Mertansine using HPLC.

Example 3

Loading Macromolecular Cargo Inside Hepatitis B Core Virus-Like Particles

The work described in this example addresses: (1) loading and retention of macromolecular cargo into VLPs and (2) specific cell targeting. For the former, examples will show loading of both nucleic acids and proteins. For the latter, prostate-specific membrane antigen (PSMA) on the surface of prostate cancer (PCa) cells will be targeted by surface modified VLPs.

Using non-natural amino acids (nnAAs) which are easily and efficiently incorporated during cell-free protein synthesis (CFPS), additional functionalities can be added onto the surface of the HepBc VLP via the "Click" reaction, including specific cell targeting using single-chain antibody fragments (scFvs) or DNA aptamers.

Additionally, cargo retention of small nucleic acids is also addressed. The assembled VLP structure is porous, containing openings with apertures up to 21 angstroms at the largest dimension. These pores are formed at the 3-fold, 5-fold, and 6-fold points of symmetry in the T=4 icosahedral structure. Small nucleic acids, for example, siRNAs may escape through these pores.

The siRNA is conjugated to the VLP after loading using disulfide bonds, to provide reliable retention while allowing release inside targeted cells. Like the disulfides that stabilize the VLP shell, the cargo-retaining disulfide bond will be broken by the reducing conditions in the cytosol, allowing the cargo to be released only in the targeted cells. In addition to the cargo loading domain on the C-terminal domain of HepBc (in the case of siRNA, containing positively charged amino acids), we also incorporated a cysteine containing a free sulfhydryl. Diamide, a mild oxidizing agent, is used to conjugate the loaded siRNA, modified to include a free sulfhydryl, to the VLP inner surface after loading the cargo.

As shown in Example 2, loading and retention mechanisms have been demonstrated using a small molecule dye, BODIPY FL-Cysteine (BDFL) that contains a free sulfhydryl. The size-exclusion chromatography (SEC) results show that the fluorescent BDFL is retained by the VLP after several wash steps that previously extracted all loaded cargo. This approach is now extended to nucleic acid cargoes.

In addition to loading siRNA through ion-pairing interactions, we also demonstrate loading siRNA through hydrophobic interactions by adding a hydrophobic "hook" to the siRNA (a cholesterol molecule). To load this siRNA construct, we used a cargo-loading domain (C-terminal HepBc extension) containing hydrophobic amino acids. Besides siRNA, these loading approaches can be extended to plasmid DNA, mRNA, and proteins (including but not limited to CRISPR Cas9). All of these cargo are larger and should not escape the VLP through the pores. For plasmid DNA and mRNA, ion-pairing cargo-loading domains may be more attractive since they are highly negatively charged. For proteins, either ion-pairing cargo-loading domains or hydrophobic cargo-loading domains can be used, targeting either surface characteristics of the proteins or C- or N-terminal extensions engineered onto the proteins. CRISPR Cas9 potentially allows a unique loading mechanism since it is actually a complex of protein and its guide RNA. As such, we can use charged cargo-loading domains that target the guide RNA in complex with CRISPR Cas9. Protein loading is demonstrated here using green fluorescent protein (GFP) for convenience in assessing loading.

Results

The following describes the design and purification of HepBc variants with altered C-terminal domains for the loading of various macromolecular cargoes, for example siRNA. For convenience, we mimic siRNAs using single-stranded DNA (ssDNA) constructs that match the same sequences (substituting thymidine for uracil) and are conjugated to the fluorescent probe 6-carboxyfluorescein (6FAM) for convenient detection.

Purification of Hepatitis B core variants with cargo loading domains. The HepBc subunit purification scheme is as described in example 1. In addition, aside from the different C-terminal cargo loading domains, we also used two variants of the HepBc shell. One takes advantage of the A131K mutation to allow VLP assembly at 0.5M NaCl or lower and will be used for loading cargo via ion-pairing attractions at lower ionic strengths. The other does not use this mutation and will be used for loading cargo via hydrophobic mechanisms at high ionic strengths (e.g. 2.5M NaCl).

A summary of the different VLP mutations and their effects follows:

The HP mutation is a series of 18 amino acid changes in each HepBc monomer that are introduced into the "spike" region that forms when monomers dimerize; this modification greatly improved the "Click" reaction for negatively charged ligands. It also reduces the immunogenicity and antigenicity of the HepBc VLPs. However, it has the undesired effect of increasing the ionic strength required for assembly from 0.5M to 1.5M NaCl.

A131K is a mutation in the assembly interface that reduced the ionic strength required for assembly of the HP variant back to the wild-type level of 0.5M NaCl (Example 1).

SS1 and SS8 are two different "SS" series mutations that each add an additional 240 disulfide bonds between VLP dimers for conditional stabilization of the VLP shell. These bonds will be reduced by the reducing conditions of the cytosol.

80M refers to the position mutated to methionine (ATG codon) in order to incorporate methionine-analog nnAAs via methionine replacement.

2ASVins inserts 3 amino acids (ASV) after the initiator formyl-methionine to allow a translation initiating non-natural methionine analog to be removed by the methionyl aminopeptidase that is provided the by the cell extract used for CFPS. This modification avoided surface conjugation to the HepBc protein N-terminus which otherwise occurs in addition to conjugation at the desired residue on the tip of the surface spike.

6H refers to the C-terminal hexahistidine tag used for purification and also for endosomal escape via the proton sponge effect.

Figures 13, 14:
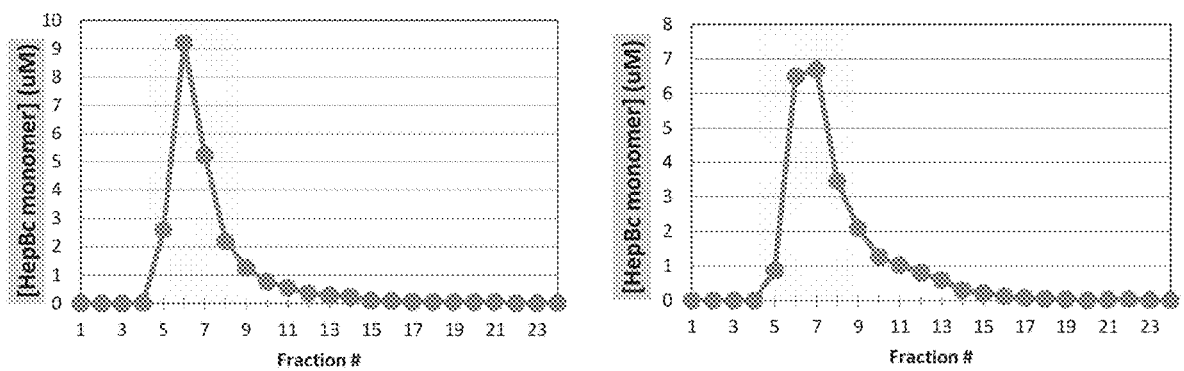
FIG. 13. SEC chromatograms showing excellent VLP assembly in solutions containing 15% DMSO (dimethylsulfoxide) with and without the presence of a 25-fold molar excess of the anti-cancer drug Mertansine.
FIG. 14. Summary of macromolecular therapeutic cargoes and the loading/retention mechanism(s) designed for each cargo.

Table 2 provides a summary of several different designs for loading macromolecular cargo. Extension refers to the C-terminal extension on the HepBc protein. Cargo refers to the entity loaded into the VLP and includes modifications to facilitate loading and retention. Entities to provide sulfhydryl groups are shown in orange, positively charges entities in red, and hydrophobic entities in green. The first column indicates the HepBc variant used for the corresponding extension/cargo pairs. FIG. 14 uses the same color scheme and provides loading domain features and loading mechanisms for a variety of macromolecular cargoes.

TABLE 2

Different HepBc VLP variants and their respective cargo

| HePBc VLP Variant | Extension | Cargo |
|---|---|---|
| HP A131K 6H | Cys | (SH)-ssDNA-(6FAM) |
| HP A131K 6H | Cys-Arg-Cys | (SH)-ssDNA-(6FAM) |
| HP 2ASVins SS1 SS8 80M 6H | (SEQ ID NO: 13 (Ile-Gly)$_2$-Ile-Cys | (SH)-ssDNA-(6FAM)-(Chol) |
| HP 2ASVins SS1 SS8 80M 6H | (SEQ ID NO: 13 (Ile-Gly)$_2$-Ile-Cys | ssDNA-(SH)-(Ile-Gly)$_2$-(6FAM) |
| HP 2ASVins SS1 SS8 80M 6H | (SEQ ID NO: 13 (Ile-Gly)$_2$-Ile-Cys | sfGFP-(Lys-Phe) |
| HP 2ASVins SS1 SS8 80M 6H | (SEQ ID NO: 13 (Ile-Gly)$_2$-Ile-Cys | sfGFP-(Lys-Phe)$_2$ |
| HP A131K 6H | (Glu)$_3$ | sfGFP-(Lys)$_6$ |
| HP A131K 6H | (Glu)$_3$ | GFP-(+36) |
| HP A131K 6H | Arg | Plasmid DNA |
| HP A131K 6H | (Arg)$_3$ | Plasmid DNA |

Purification of HepBc variants from the CFPS product mixture was occasionally hindered by premature VLP assembly that caused the hexahistidine purification tags to be inaccessible. By adding a reducing agent to the CFPS reaction (4 mM reduced glutathione (GSH)) and reducing the ionic strength by including 50 mM Kglutamate instead of the standard 175 mM concentration, subunit purification and subsequent cargo loading was improved. In some cases, the A131K variant was used without the SS1 and SS8 mutations. See Table 3 for the NaCl concentrations used to assemble each variant and the extent of VLP assembly.

TABLE 3

Assembly conditions and results for representative HepBc derivatives.

| HepBc Variant | HP A131K 6H | | | | | HP 2ASVins SS1 SS8 80M 6H |
|---|---|---|---|---|---|---|
| Extension | C | CRC | R | RRR | EEE | IGIGIC |
| [NaCl] (M) | 0.5 | 0.5 | 0.5 | 0.5 | 0.5 | 2.5 |
| % Assembly | 66.0 ± 3.4 | 40.3 ± 1.6 | 41.1 ± 1.9 | 40.9 ± 4.3 | 71.9 ± 0.4 | 62.5 ± 1.1 |

NaCl concentrations used to assemble HepBc variants with different cargo loading extensions and the extent of their VLP assembly. Assembly percentage is shown as the mean of repeated experiments ± the standard deviation (n = 3).

Figure 15A:
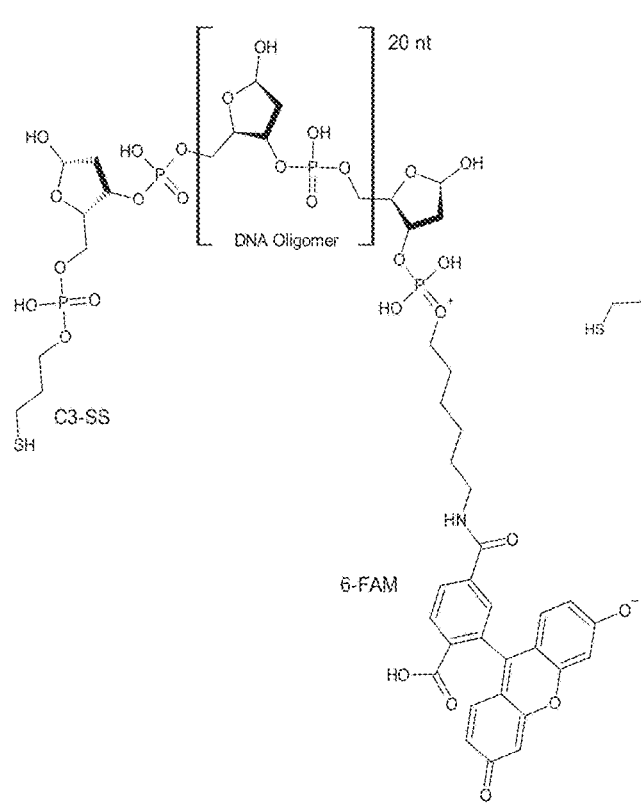
FIG. 15A-15B. 22 nt single-stranded DNA (ssDNA) constructs.
Figure 15B:
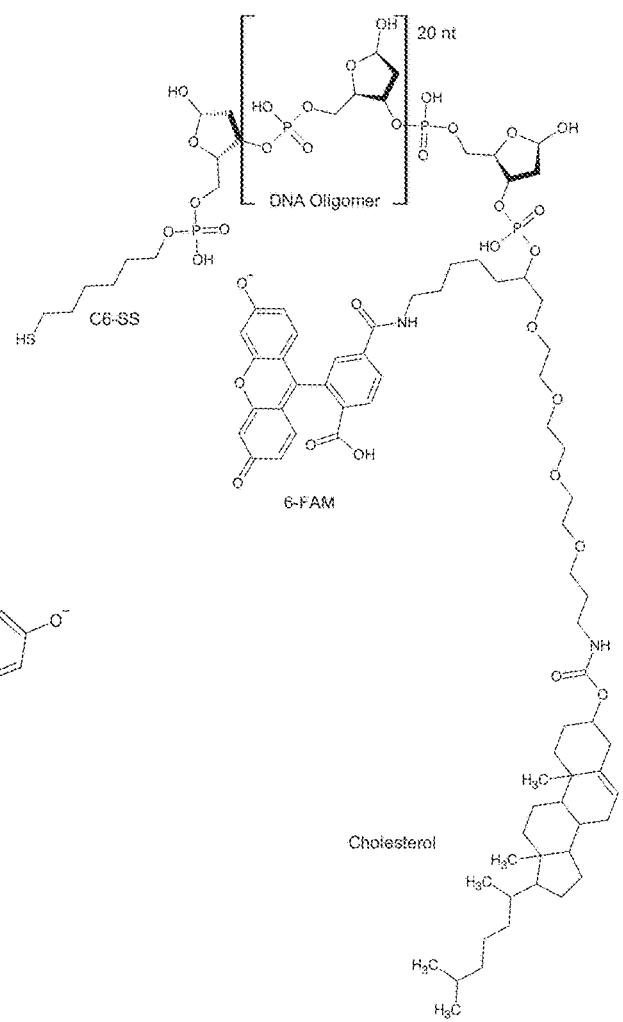

Loading nucleic acids. This example describes the loading of a nucleic acid using two different adsorption principles, ion pairing and hydrophobic attraction. As described, a ssDNA is used to mimic an siRNA and two different ssDNA constructs are used: SH-ssDNA-6FAM for ion pairing mediated loading and SH-ssDNA-6FAM-Chol for hydrophobicity mediated loading. These are diagrammed in FIG. 15. SH refers to the free sulfhydryl attached to the ssDNA after either a three- or six-carbon chain; 6FAM refers to 6-carboxyfluoresceine, a fluorescein derivative and fluorescent probe conjugated to the ssDNA for convenient detection; and Chol refers to cholesterol with a triethylene glycol (TEG) spacer used to provide a hydrophobic loading "hook". The actual sequence of the 22 nt ssDNA sequence mimics a known anti-PCa siRNA against the androgen receptor. The free sulfhydryl modification allows conditional conjugation to the VLP interior surface after loading to prevent escape through the VLP pores. The fluorescent modification is only for tracking during loading and delivery will not be present in the final siRNA therapeutic. The two constructs differ in the presence or absence of the cholesterol-TEG hydrophobic loading "hook".

Figure 16:
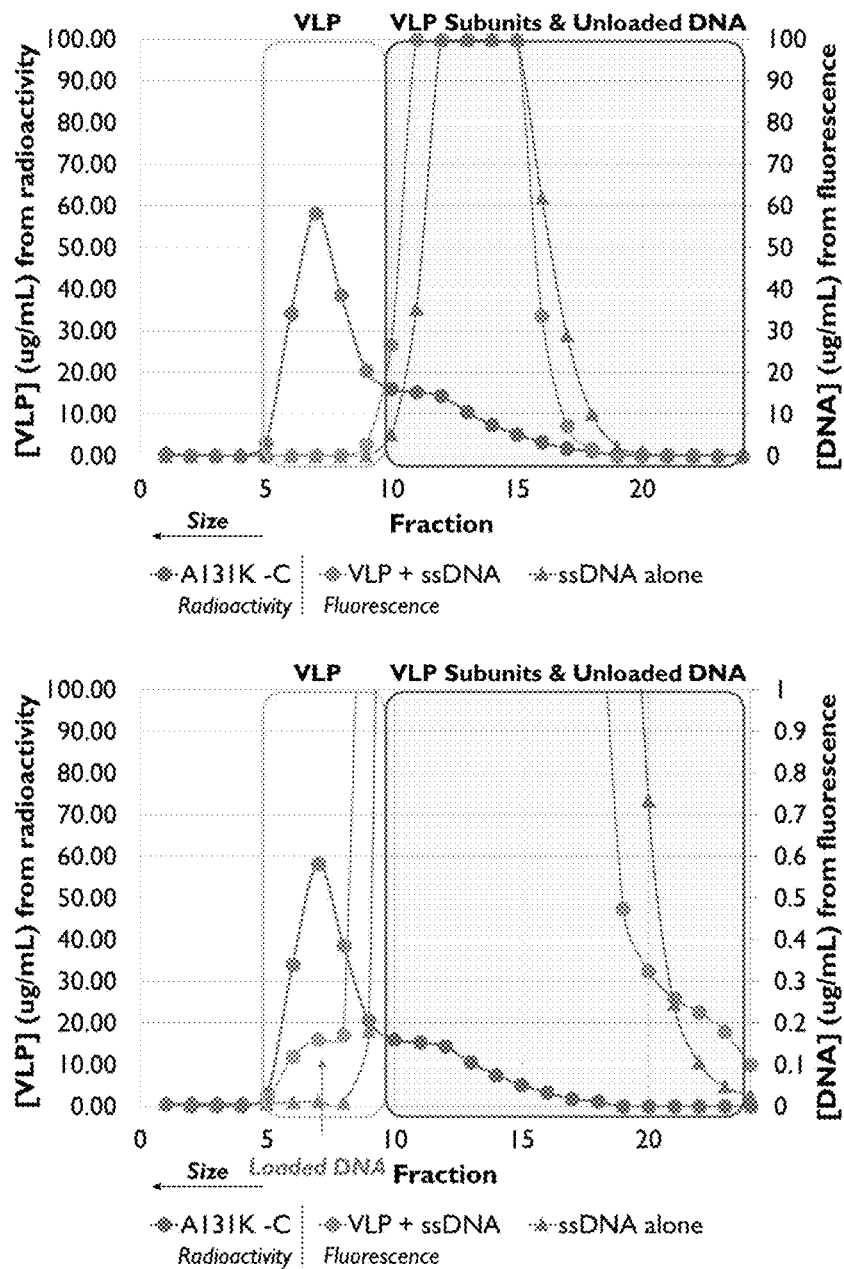
FIG. 16. Loading single-stranded DNA (ssDNA) using a neutral loading domain on HepBc (Cys). The size-exclusion chromatograms show VLP and ssDNA concentrations. The top chart is the full ssDNA profile and the bottom chart reduced the [DNA] ordinate to show the ssDNA associated with the VLP. Experiments used HepBc HP A131K 6H with loading domain —C.
Figure 17:
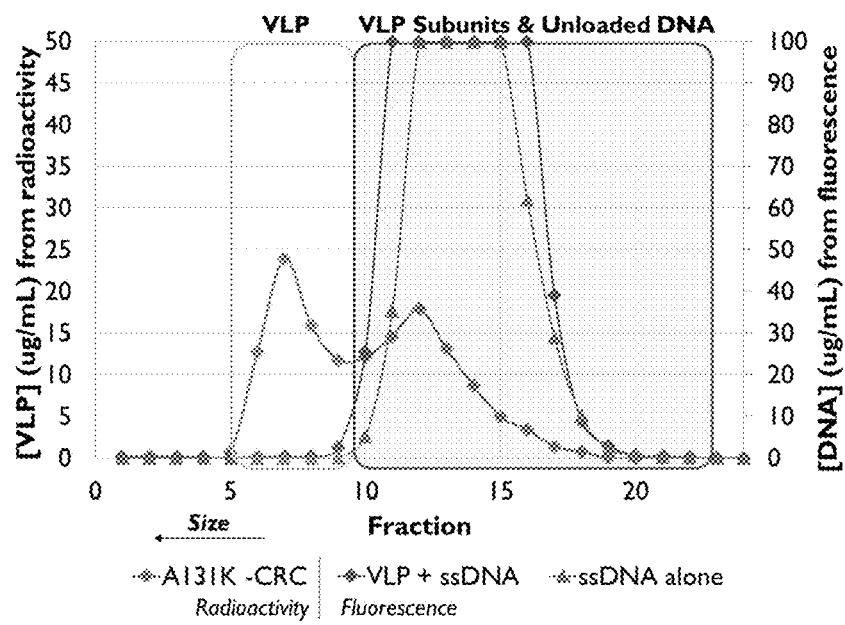
FIG. 17. Loading single-stranded DNA (ssDNA) using an ion-pairing loading domain on HepBc (Cys-Arg-Cys). The size-exclusion chromatograms show VLP and ssDNA concentrations. The top chart is the full ssDNA profile and the bottom chart reduced the [DNA] ordinate to show the ssDNA associated with the VLP. Experiments used HepBc HP A131K 6H with loading domain —CRC.
Figure 17:
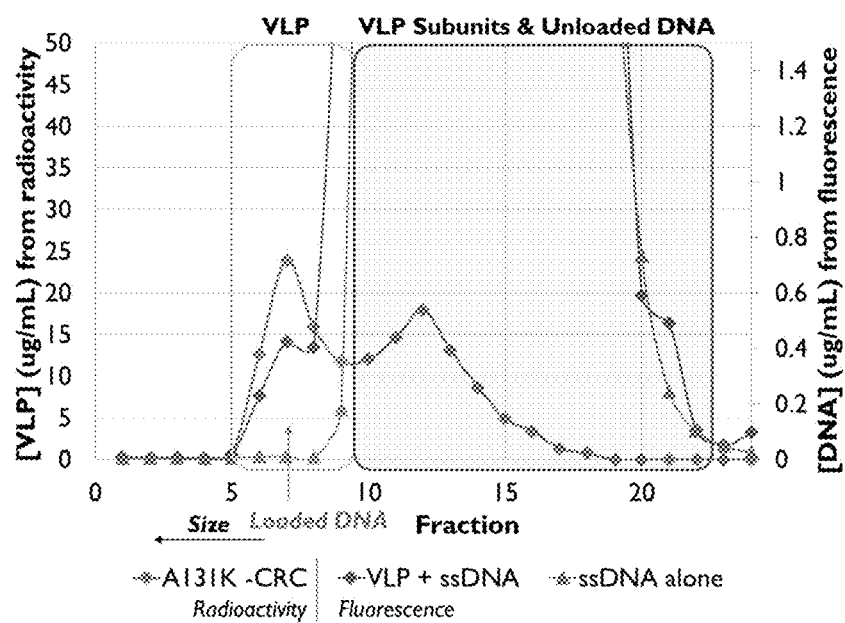
Figure 18:
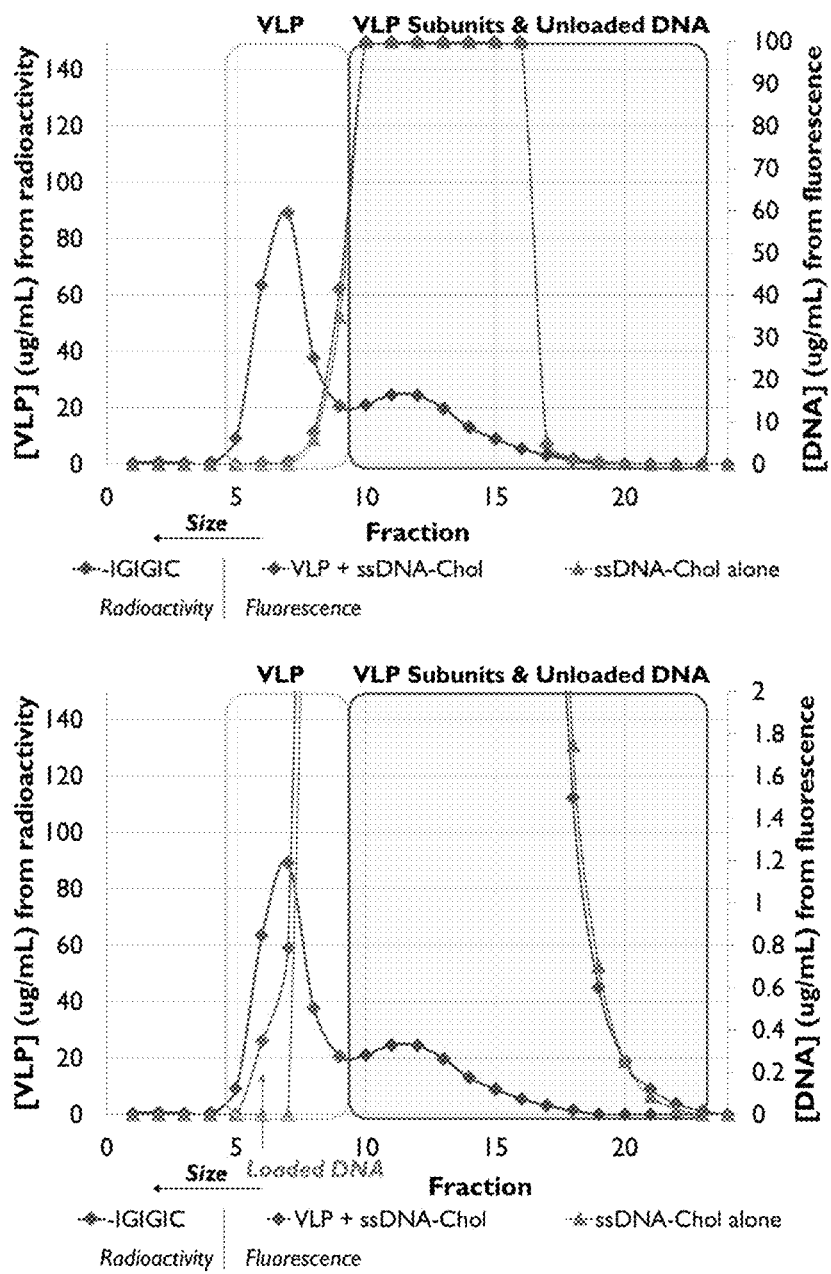
FIG. 18. Loading single-stranded DNA (ssDNA) using a hydrophobic loading domain on HepBc (Ile-Gly-Ile-Gly-Ile-Cys). The size-exclusion chromatograms show VLP and ssDNA concentrations. The top chart is the full ssDNA profile and the bottom chart reduced the [DNA] ordinate to show the ssDNA associated with the VLP. Experiments used HepBc HP 2ASVins SS1 SS8 80M 6H with loading domain -IGIGIC.

Cargo loading is performed by adding the desired cargo to the purified HepBc subunits, allowing the mixture to associate at equilibrium, and inducing concurrent cargo loading and VLP assembly by increasing the ionic strength to 0.5M for loading via ion-pairing interactions (in this case, loading SH-ssDNA-6FAM) or to 2.5M NaCl for loading via hydrophobic interactions (in this case, loading SH-ssDNA-6FAM-Chol). Size-exclusion chromatography (SEC) is used to separate VLPs from unassembled subunits and also from unloaded DNA. Each fraction is analyzed for radioactivity to determine the presence of HepBc protein and for fluorescence to determine the presence of ssDNA cargo. At 1-2 µg/mL DNA, a significant increase in fluorescence associated with the VLP peak is seen. Two different A131K HepBc variants, containing either a Cys or Cys-Arg-Cys cargo loading/retention domain, were loaded at 0.5M NaCl (FIGS. 16 and 17). SH-ssDNA-6FAM-Chol was loaded into a HepBc variant containing an (Ile-Gly)$_2$-Ile-Cys cargo loading/retention domain, but lacking the A131K mutation, at 2.5M NaCl. Although only 1.5M NaCl is required to assemble this VLP, increasing the ionic strength increases the driving forces for cargo loading (FIG. 18).

Figure 19:
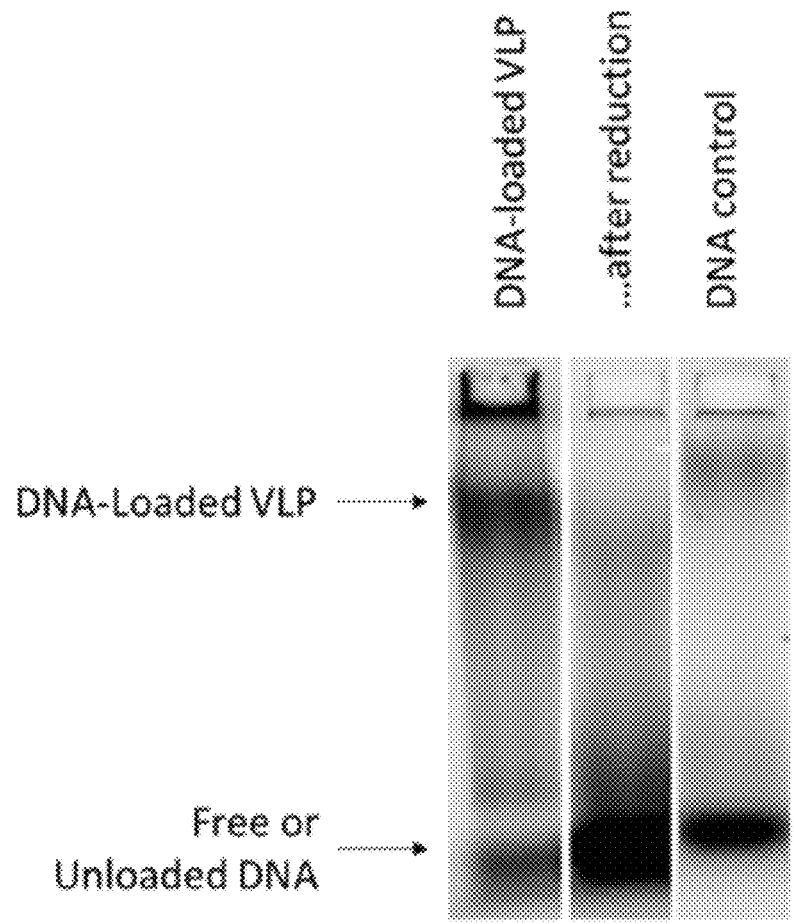
FIG. 19. Agarose gel electrophoresis analysis of ssDNA loading into HepBc VLPs. DNA is visualized by fluorescence of the attached fluorophore. DNA loaded VLPs were applied to the first lane while the second lane shows results after the VLPs have been reduced to release the cargo. The third lane shows the cargo before loading for comparison.

Given the proximity of unloaded ssDNA to the loaded ssDNA in the above SEC results, we employed additional methods to verify that the VLPs were loaded with ssDNA. First, native agarose gels (lacking ethidium bromide, urea, SDS, or any loading dyes) were used to separate ssDNA loaded inside VLPs from unloaded ssDNA and were visualized using a General Electric (GE) Typhoon flatbed fluorescent scanner (since the ssDNA constructs are fluorescent). As FIG. 19 indicates, ssDNA inside the VLPs is significantly upshifted compared to free ssDNA. In addition, after reduction, the ssDNA is released from the assembled VLPs and matches the electrophoretic mobility of the free ssDNA, suggesting the disulfide bond-based conjugation of the cargo is necessary. Additionally, we "washed" the samples to remove unloaded ssDNA and verify that ssDNA was loaded and retained. Samples were first diluted 15-fold and subsequently concentrated (retaining the VLPs, but removing unloaded ssDNA) using 50 kDa molecular weight cutoff (MWCO) Amicon® Ultra Centrifugal Filters (VLP molecular weight is 4.3 MDa and the ssDNA is 8 kDa).

Figure 20:
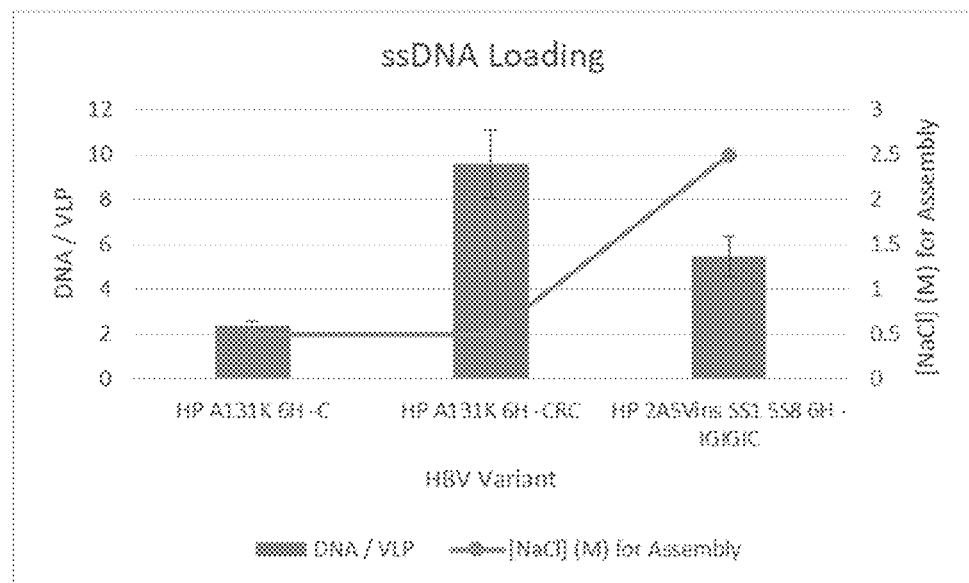
FIG. 20. Summary of ssDNA loaded per VLP for various HepBc VLP variants. Error bars represent standard deviation from the mean (n=3) of repeated experiments.

The molecules of ssDNA loaded per individual VLP were calculated for each fraction of the SEC data before and after the "wash" step (FIG. 20). The highest loading was obtained with HepBc HP A131K 6H-CRC VLPs using SH-ssDNA-6FAM (about 10 per VLP), but the hydrophobicity-based loading was similar (about 6 per VLP). Passive loading with HP A131K 6H-C was significantly lower (about 2 per VLP), which suggests that the cargo loading domain designs are beneficial. These values are higher than any currently published results for loading siRNA inside HepBc VLPs (highest published is 4 siRNA/VLP).

Loading proteins. To demonstrate protein loading inside VLPs, we used superfolder GFP (sfGFP) for convenient detection of loading and added C-terminal polypeptide extensions with displaying lysine and phenylalanine to provide hydrophobic attractions to a IGIGIC C-terminal extension on the HepBc protein.

Figure 21:
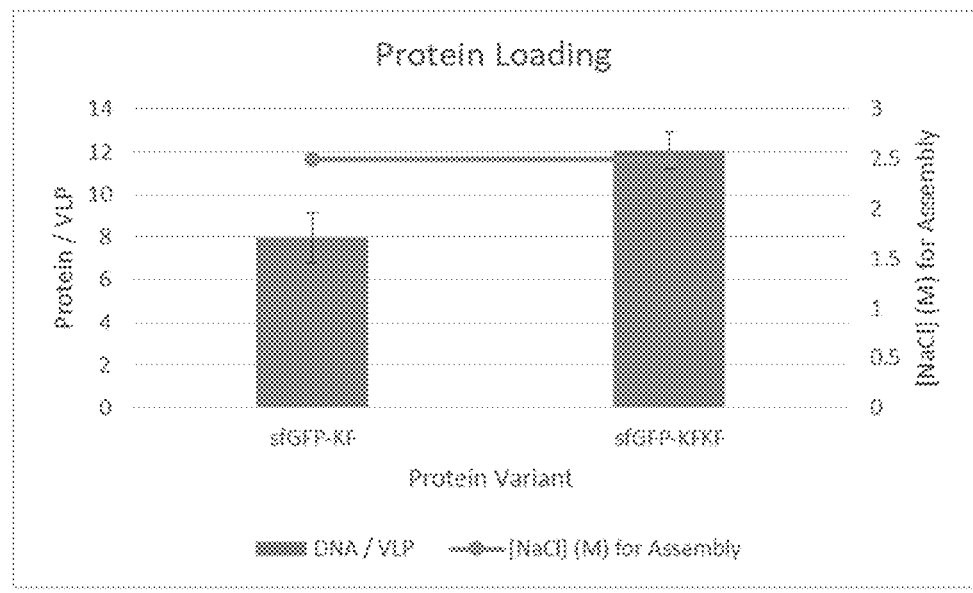
FIG. 21. Summary of proteins loaded per VLP for various HepBc VLP variants. Error bars represent standard deviation from the mean (n=3) of repeated experiments.

Either sfGFP-KF or sfGFP-KFKF was added to purified HepBc HP 2ASVins SS1 SS8 80M 6H-IGIGIC subunits and assembly was triggered by 2.5 M NaCl. SEC was used to separate VLPs from unassembled HepBc subunits and unloaded proteins. Each fraction was analyzed for radioactivity to determine the concentration of HepBc protein and for fluorescence to determine the amount of the sfGFP-KF or sfGFP-KFKF cargo. A summary of loading results is shown in FIG. 21.

Figure 22:
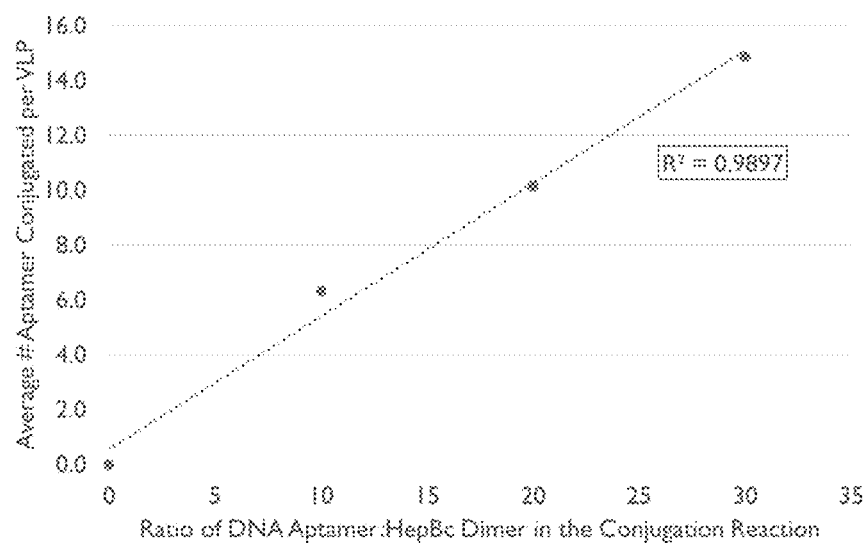
FIG. 22. Varying the number of anti-PSMA DNA aptamers attached to each HepBc VLP using HepBc HP SS1 78AHA 6H.

Specific cell targeting & cargo delivery. To enable specific targeting, the "Click" reaction was used to display anti-PSMA DNA aptamers on the surface of the VLP as previously described. The anti-PSMA DNA aptamer was previously described (Boyacioglu et al. Mol. Ther.—Nucleic Acids 2, e107 (2013)). The construct used here only contains a single aptamer domain extended with an alkyne for conjugation to the VLP (which displays azidohomoalanine, AHA). Using previously developed methods for attaching ligands to the VLP via the "Click" reaction we can display up to 15 copies of the aptamer per VLP (FIG. 22).

To show that VLPs displaying this aptamer are capable of binding PCa (prostate cancer) cells specifically, we employed a cell-binding assay using LNCaP (PSMA+) cells and PC-3 (PMSA−) cells. The cells were detached from their culture plates, washed, and resuspended in phosphate-buffered saline (PBS) with 1% bovine serum albumin (BSA). Different concentrations of radioactive VLPs displaying the anti-PSMA DNA aptamer were added to the cells and were allowed to incubate for 3 hr at 4° C. After the incubation, the cells were pelleted and the supernatant was sampled for remaining VLP via radioactivity. By calculating the concentrations of VLPs associated with the cells, we estimated the binding affinity. Specifically, the VLPs show strong avidity for LNCaP (PSMA+) cells ($K_D$=4.6 nM), similar to the affinity of several anti-PSMA antibodies ($K_D$=1.8, 11, 18 nM), and negligible PC-3 (PSMA−) cell binding was observed. In addition, by analyzing the asymptote, the binding capacity of LNCaP cells was determined to be roughly 4-5 million VLPs, on the same order as PSMA/cell, indicating maximum binding capacity.

Figure 23:
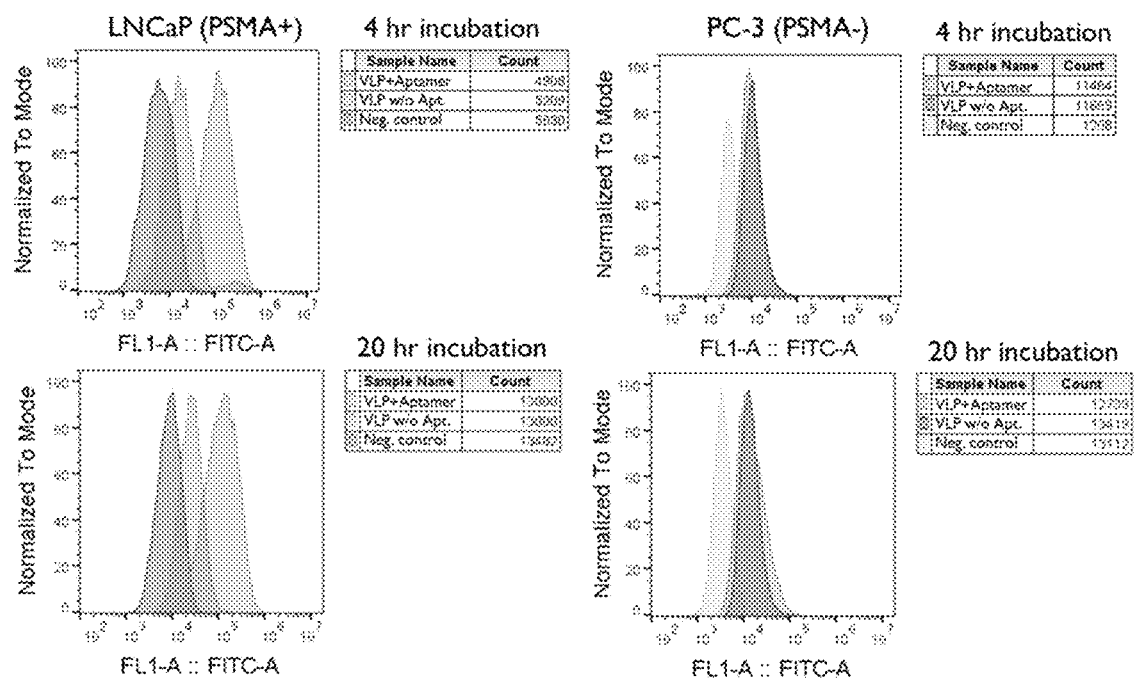
FIG. 23. Flow cytometry analysis of VLP association with LNCaP cells. Although there is some non-specific binding as seen with VLPs lacking aptamer and with PC-3 cells, VLPs displaying the aptamer associate to a greater extent with PSMA+LNCaP cells. Count refers to the number of cells analyzed for each sample.

Cell targeting specificity was then analyzed using a CytoFlex flow cytometer. First, VLPs loaded with fluorescent BDFL, with and without the attached aptamer, were added to adherent LNCaP or PC-3 cells at 37° C. The cultures were allowed to incubate for 4 or 20 hrs and were subsequently detached and washed with PBS with 10% fetal bovine serum (FBS). The cells were then analyzed by the flow cytometer and the fluorescence associated with each living cell was determined for each sample. Results are shown in FIG. 23. Although there is some non-specific binding as seen with VLPs lacking aptamer and with PC-3 cells, VLPs displaying the aptamer show significantly more binding to PSMA+ LNCaP cells.

Cell targeting specificity was also analyzed using a Nikon Ti-E inverted epifluorescence microscope by adding VLPs loaded with fluorescent BDFL, with and without the aptamer, to adherent LNCaP or PC-3 cells at 37° C. The cultures were allowed to incubate for 4 hrs before removing the media and washing with PBS with 0.01% Tween-20. The live cultures were then imaged. The results support the flow cytometry results as some non-specific binding is seen with PC-3 cells, but significantly more binding is seen with LNCaP cells.

Nikon Ti-E inverted epifluorescence microscope. A more stringent assay was performed by adding VLPs loaded with fluorescent BDFL, with and without the aptamer, to adherent LNCaP or PC-3 cells at 37° C. The cultures were again allowed to incubate for 4 hrs before removing the media. This time, however, the cells were washed with 0.5% acetic acid with 500 mM NaCl. This has been used before to remove surface-bound proteins to help determine if the therapeutic is being endocytosed. The live cultures were then imaged using an epifluorescence microscope. The results here show that the receptor-mediated internalization only occurs with VLPs displaying the aptamer and LNCaP cells. PC-3 cells and VLPs without the aptamer show negligible amounts of internalization.

The work presented herein examines the influence of changes to the outer and inner surface of the VLP shell. The outer surface was modified by incorporated AHA at position 80 in the HepBc protein and using "Click" chemistry to display anti-PSMA DNA aptamers. The inner surface was modified by mutating the C-terminal domain to allow loading of different cargo. Combining the modifications to all three layers will allow this novel nanoparticle to be used as a highly effective, targeted treatment for many diseases.

Although PCa is used as a model disease target, the platform is useful to develop treatments for a number of diseases. By separating the functionalities of the vehicle into three distinct layers, we can separately modify the VLPs to alter the disease target, the therapeutic cargo, or the assembly requirement. As shown here, aptamer-based targeting can be highly effective, but this system can also easily use protein-based targeting agents such as antibody fragments or scFvs.

The cargo loading work focused on loading different types of cargo (proteins and nucleic acids) and on using different loading mechanisms (ion-pairing attraction or hydrophobicity-based methods). The results indicate feasibility for loading new therapeutics based on their surface characteristics or the influence of simple loading tags. The development of disulfide bond-based retention mechanisms will also broaden the size range of cargo that can be loaded.

This work can be extended for many therapeutic cargoes, such as siRNAs to silence genes such as prohibitin 1, androgen receptor, EGFR, and survivin and to proteins such as granzyme B to induce apoptosis.

Materials and Methods

VLP mutagenesis study. The various HepBc and GFP variants used in this study for loading were produced using QuikChange mutagenesis and primers from IDT. The sequences were verified through DNA sequencing by Sequetech.

Cell-free protein synthesis reactions. Initial expression reactions for HepBc proteins used the PANOx-SP cell-free protocol as previously described. Cell extracts were prepared from A19 mer, AtonA, AtnaA, AspeA, AendA, AsdaA, AsdaB, AgshA E. coli cells (strain KC6) grown in a Braun 10 L Biostat C fermenter. In addition to this extract, the small molecule reagents necessary for protein synthesis, purified T7 RNA polymerase, and the plasmid of interest were added. The plasmid was prepared using Qiagen Maxiprep purification kits and included an isopropanol/ethanol wash step. In addition to the standard amino acids, we also added 5 µM of $^{14}$C-leucine to enable quantification of the synthesized protein by measuring incorporated radioactivity. The PanOx-SP reactions were performed at multiple scales: 50 µL in 2 mL Eppendorf tubes, 600 µL in sealed 6-well tissue culture plates, or 6 mL in sealed 10 cm petri dishes. The reactions were incubated at 20-30° C. for various times. Protein concentrations were determined by measuring the incorporated radioactivity using liquid scintillation counting. Total product samples were measured directly and soluble product samples were measured after removing insolubles with centrifugation at 10 k×g for 15 min. Both samples are precipitated on Whatman filter paper with 5% trichloroacetic acid (TCA) before being washed three times with 5% TCA to remove unincorporated $^{14}$C-leucine. In some cases, the normal 175 mM Kglutamate concentration was reduced to 50 mM for protein synthesis at lower ionic strength to avoid premature HepBc subunit association.

VLP purification method. HepBc proteins were expressed using standard cell-free protein synthesis reactions as described above. The insolubles were removed using centrifugation at 10 k×g for 15 min. The improved purification strategy first used Sephadex G25 resin to exchange the samples into 50 mM Tris, 25 mM Imidazole, 0.1% Tween-20, pH 7.4 before loading the soluble fraction onto Ni-NTA resin. After loading onto the Ni-NTA column, the samples were the washed with 4 column volumes (CVs) of 50 mM Tris, 25 mM Imidazole, 0.1% Tween-20, pH 7.4 and eluted with 5 CVs of 50 mM Tris, 250 mM Imidazole, 0.1% Tween-20, pH 7.4. Elution fractions containing HepBc subunits were then again applied to Sephadex G25 resin (2.5 mL of sample loaded onto 8.3 mL of resin) to remove imidazole and exchange into 50 mM Tris, 0.1% Tween-20, pH 7.4. Samples were concentrated using stirred cell concentrators or ultrafiltration-based centrifugal concentrators using 3 kDa molecular weight cutoff filters from Millipore. VLP assembly was induced by directly adding 0.5-2.5M NaCl from a stock solution of 50 mM Tris, 5M NaCl, 0.1% Tween-20, pH 7.4. Assembled VLPs were quantified and purified by applying 200 µL of the samples to 2.2 mL Sepharose 6 Fast Flow size-exclusion column, applying the assembly buffer, and collecting 24×150 L fractions. Protein concentration in each fraction was determined by measuring the radioactivity using liquid scintillation counting. The first peak (typically between fractions 5 and 10) was collected as the VLPs. These VLPs were subsequently oxidized using 20-50 mM diamide to form the stabilizing disulfide bonds. The diamide was then removed by using Sephadex G25 resin to exchange the samples into 50 mM Tris, 0.1% Tween-20, pH 7.4.

Modified VLP expression methods to reduce premature assembly. Two major changes were made to reduce premature VLP assembly. First, the cell-free protein synthesis reactions were altered to contained lower ionic strengths (90 mM instead of 215 mM) by reducing the potassium glutamate from 175 mM to 50 mM. The second change was to add 4 mM reduced glutathione to the cell-free protein synthesis reactions to prevent disulfide bond formation.

SDS-PAGE and autoradiogram analysis of premature VLP assembly. Protein size was analyzed by sodium dodecyl sulfate-polyacrylamide gel electrophoresis (SDS-PAGE) and autoradiography. NuPAGE Novex precast gels and reagents were purchased from Invitrogen (Carlsbad, Calif.). Samples were denatured for 10 min at 90° C. in loading buffer (1×LDS loading buffer and 50 mM dithiothreitol). The samples were loaded onto a 10% (w/v) Bis-Tris precast gel with a separate lane for the Mark 12 molecular weight protein standard, and electrophoresed in MES/SDS running buffer. SimplyBlue SafeStain was used to stain and fix the gels according to the manufacturer's recommendations. The gels were dried using a gel dryer model 583 (Bio-Rad, Richmond, Calif.), before exposure to a storage phosphor screen (Molecular Dynamics), which was subsequently scanned using a Typhoon Scanner (GE Healthcare).

Loading cargo inside VLPs. Before inducing self-assembly by adding NaCl, HepBc monomers were incubated with desired cargo at room temperature for 30 min. HepBc monomers were 10-50 µM and cargo was added at 20-500 µM. After inducing self-assembly by adding 0.5-2.5M NaCl as described above, loading was determined first by applying 200 µL of the samples to 2.2 mL Sepharose 6 Fast Flow size-exclusion chromatographic resin and eluting 24×150 µL fractions with the assembly buffer. HepBc concentration in each fraction was determined by measuring the radioactivity using liquid scintillation counting. Cargo concentration in each fraction was determined by measuring the fluorescence using a 96-well fluorimeter. The first peak (typically between fractions 5 and 10) was collected as the VLPs and quantified for loading.

ssDNA-loaded samples were also analyzed using native agarose gel electrophoresis. 15 µL of each sample was loaded into a 1% agarose gel in TBE buffer. 100V were applied to the gel for 45 minutes and gels were imaged for fluorescence using a Typhoon Scanner (GE Healthcare). Samples were also diluted 15-fold and concentrated back to the 1× concentration using ultrafiltration membranes. 50 kDa molecular weight cutoff (MWCO) Amicon® Ultra Centrifugal Filters were used to remove unloaded ssDNA (VLP molecular weight is 4.3 MDa and the ssDNA is 8 kDa). Samples were then analyzed for radioactivity using liquid scintillation counting and fluorescence using a fluorimeter to quantify loading.

Surface functionalization through the "Click" reaction. The surfaces of purified and oxidized VLPs were modified by conjugating a DNA aptamer onto their surface through the copper(I)-catalyzed cycloaddition reaction (also known as the "Click" reaction). 40-85 nM HepBc VLPs were combined with 10-100 µM ligand, 0.5 mM tris(triazolylmethyl) amine, 0.01% Tween-20, and 2 mM tetrakis copper(I) in 50 mM phosphate buffer at pH 8 and allowed to react for 4-16 hr anaerobically. Copper(I) and un-conjugated ligands were removed using Sepharose 6 Fast Flow size-exclusion chromatographic resin, as described above for VLP purification. The extent of conjugation was determined by sodium dodecyl sulfate-polyacrylamide gel electrophoresis (SDS-PAGE) and autoradiography (data not shown). NuPAGE Novex precast gels and reagents were purchased from Invitrogen (Carlsbad, Calif.). Samples were denatured for 10 min at 90° C. in loading buffer (1×LDS loading buffer and 50 mM dithiothreitol). The samples were loaded onto a 10% (w/v) Bis-Tris precast gel with a separate lane for the Mark 12 molecular weight protein standard, and electrophoresed in MES/SDS running buffer. SimplyBlue SafeStain was used to stain and fix the gels according to the manufacturer's recommendations. The gels were dried using a gel dryer model 583 (Bio-Rad, Richmond, Calif.), before exposure to a storage phosphor screen (Molecular Dynamics), which was subsequently scanned using a Typhoon Scanner (GE Healthcare).

Cell-culture. Prostate cancer cell lines (LNCaP and PC-3) were cultured in DMEM (Life Technologies) with 10% FBS (Alstem), 1% penicillin (Life Technologies), and 1% streptomycin (Life Technologies). Cells were grown at 37° C. with 5% $CO_2$. Depending on the experiment, cells were seeded in 96-well plates or 6-well plates and grown for two days prior to use.

Radioligand cell-binding assay. Cells were seeded in 6-well plates two days prior to incubating with VLPs. LNCaP cells were seeded at 300,000 cells per well and PC-3 cells were seeded at 125,000 cells per well. The media was aspirated and the cells were detached by incubating with 0.5 mM EDTA in PBS at 37° C. for 10 min. Cells were transferred to Eppendorf tubes, pelleted, and washed twice with PBS with 1% BSA. Samples containing 100,000 cells were then incubated with 0 to 100 nM of VLPs displaying anti-PSMA DNA aptamers (15 aptamers/VLP). Cells were allowed to incubate for 3 hr at 4° C. to reduce internalization. After, the cells were pelleted and the supernatant was aspirated. VLP concentration in the supernatants was determined by measuring the radioactivity using liquid scintillation counting.

Flow cytometry. Cells were seeded in 6-well plates two days prior to incubating with VLPs. LNCaP cells were seeded at 300,000 cells per well and PC-3 cells were seeded at 125,000 cells per well. After two days, VLPs displaying anti-PSMA DNA aptamers (15 aptamers/VLP) were added to each well at 9 nM and allowed to incubate for 4 hr at 37° C. After incubation, the media was aspirated and the cells were detached by incubating with 0.5 mM EDTA in PBS at 37° C. for 10 min. Cells were transferred to Eppendorf tubes, pelleted, and washed twice with PBS with 10% FBS. Cells were resuspended in 200 µL PBS with 10% FBS and transferred to tubes through a 0.35 micron filter. Samples were then analyzed using a CytoFlex flow cytometer with medium flow rate and counting more than 4000 live cells per sample. Data was analyzed with FlowJo.

Fluorescence microscopy. LNCaP cells were seeded at 10,000 cells per well and PC-3 cells were seeded at 3,000 cells per well two days prior to incubating with VLPs. After two days, VLPs displaying anti-PSMA DNA aptamers (15 aptamers/VLP) were added to each well at 9 nM and allowed to incubate for 4 hr at 37° C. After incubation, the media was aspirated and the cells were washed twice with PBS with 10% FBS. Images were taken of the cultures in 96-well plates with a Nikon Ti-E inverted epifluorescence microscope.

Example 4

Improved Virus-Like Particle Stabilization

This example describes a stabilized virus like particle using a double disulfide bridge network. This prevents the nanoparticle from disassembling to form smaller sub-units in low ionic strength buffers under slightly reducing conditions.

A virus like particle (VLP) mutant is provided that has enhanced solution stability in mildly reducing conditions. This is achieved by combining two disulfide bridges connecting each of the 240 VLP subunits. This builds on a D29C-R127C disulfide pair that was previously introduced in the VLP protein, by adding a P134C-N136C pair, which stabilizes the VLP subunits closer to the C-terminus. The double disulfide bridged mutant is more strongly stabilized over mildly reducing conditions that are required in the downstream functionalization of these particles.

VLPs stabilized by a single sulfide bridge were found to disassemble over the mildly reducing environment of the Cu(I) catalyzed 'Click' reaction. This reaction is a convenient methods for functionalizing the VLP scaffold. A VLP that remains assembled is highly desirable.

Coomassie stained non-reducing SDS-PAGE gel was performed on a single disulfide network stabilized HBc variant after undergoing exposure to the mildly reducing conditions of the anaerobic Cu(I) catalyzed conjugation reaction. The VLP has become unstable as subunits of the VLP were observed to migrate into the gel. The fully stabilized, assembled VLP is too large to migrate into the gel. The double disulfide network stabilized HBc variant was exposed to the same mildly reducing conditions of the Cu(I) catalyzed conjugation reaction. Even using the more sensitive autoradiogram, destabilized subunits are not observed.

Methods:

The Hepatitis B core (HBc) protein was expressed using the PANOx-SP cell free platform as previously described. HBc was prepared using cell extracts of the KC6 strain (A19 met+, ΔtonA, ΔtnaA, ΔspeA, ΔendA, ΔsdaA, ΔsdaB, ΔgshA). Cell extract was prepared either using a Braun 10 L Biostat C fermenter or using shake flask cultures. In addition to this extract, the small molecule reagents necessary for protein synthesis (10 mM magnesium glutamate, 10 mM ammonium glutamate, 175 mM potassium glutamate, 1.25 mM ATP, 1 mM GTP, 1 mM UTP, 1 mM CTP, 34 µg/mL folinic acid, 170.6 µg/mL tRNA, 2 mM of each of the 20 natural amino acids excluding glutamate, 30 mM phosphoenolpyruvate, 0.33 mM NAD, 0.27 mM CoA, 2.7 mM oxalic acid, 1 mM putrescine, and 1.5 mM spermidine), purified T7 RNA polymerase, and the plasmid of interest were added. The plasmid was the last component added to the reaction. The plasmid was prepared using Qiagen Maxiprep purification kits which includes an isopropanol/ethanol wash step. In addition to the standard amino acids, 5 µM of 14C-leucine was also added to enable quantification of the synthesized protein by measuring incorporated radioactivity.

The reactions were performed at multiple scales: 50 µL in 1.5 mL Eppendorf tubes, 500 µL to 1 mL in sealed 6-well tissue culture plates, or 3-6 mL in sealed 10 cm petri dishes. The reactions were incubated at 30° C. for 6 hr. Protein concentrations were determined by measuring the incorporated radioactivity using liquid scintillation counting (Beckman LS6000 SC). Total proteins samples were measured directly, and soluble protein samples were measured after removing insoluble proteins by centrifugation at 10 k rcf for 15 min. Both samples were precipitated on Whatman filter paper before being washed three times with 5% trichloroacetic acid to remove unincorporated 140-leucine.

The purification strategy first used Sephadex G25 resin (General Electric) to exchange the samples into 50 mM Tris, 25 mM Imidazole, 0.1% Tween-20, pH 7.4 before loading the soluble fraction onto an equal volume of Ni-NTA resin (Qiagen). The insoluble proteins were removed using centrifugation at 10 k rcf for 15 min. After loading onto the Ni-NTA column, the samples were the washed with 5 column volume (CV) of 50 mM Tris, 25 mM Imidazole, 0.1% Tween-20, pH 7.4 and eluted in 0.5 CV fractions (4 CV total) of 50 mM Tris, 250 mM Imidazole, 0.1% Tween-20, pH 7.4. Samples were analyzed for HBc proteins by measuring the incorporated radioactivity using liquid scintillation counting. Samples with HBc proteins were then again applied to Sephadex G25 resin to remove imidazole and exchange them into 50 mM Tris, 0.1% Tween-20, pH 7.4. Samples were then concentrated using stirred cell concentrators or ultrafiltration-based centrifugal concentrators using 3 kDa molecular weight cutoff filters from Millipore. VLP assembly was induced by a salt spike to a final concentration of 1.5M NaCl from a stock solution of 50 mM Tris, 5M NaCl, 0.1% Tween-20, pH 7.4. Assembled VLPs were quantified and purified by applying 200 uL of the samples to 2.2 mL Sepharose 6 Fast Flow (General Electric) size-exclusion chromatographic resin, eluting 18×150 uL fractions. Protein concentration in each fraction was determined by measuring the radioactivity using liquid scintillation counting. Two peaks were obtained: VLPs between fractions 5 and 10 and unassembled HBc proteins between fractions 11 and 18. The assembly percentage was then calculated using the areas under the curves (AoC):

$$\text{Assembly \%} = \frac{AoC_{F5-10}}{AoC_{F5-18}} * 100$$

The mutations were made using Quikchange site directed mutagenesis. The following primer, along with its reverse complement, were used in the Quikchange reactions to change amino acid residues at positions 134 and 136:

SS8 Forward Primer (Mutated Nucleotides in Bold) (SEQ ID NO:14)

```
GGATTTGTACTCCGCCGGCTTACCGTTGTCCGTGCGCACCGATCCTGAGCACCC
TGCCG
```

| Reference Sequences | | |
|---|---|---|
| Wild-type (HBc149) | MDIDPYKEFGATVELLS FLPSDFFPSVRDLLDTA AALYRDALESPEHCSPH HTALRQAILCWGDLMTL ATWVGTNLEDPASRDL VVSYVNTNVGLKFRQLL WFHISCLTFGRETVLEY LVSFGVWIRTPPAYRPP NAPILSTLPETTVV (SEQ ID NO: 1) | ATGGATATCGACCCGTACAAAGAATTCGGCGCGACCG TTGAACTGCTGTCTTTCCTGCCGTCTGATTTCTTCCCG TCTGTTCGTGACCTGCTGGACACCGCGGCAGCACTGT ACCGTGACGCGCTGGAATCTCCGGAACATTGTTCTCC GCATCACACTGCGCTGCGTCAGGCGATTCTGTGCTGG GGCGACCTGATGACCCTGGCGACTTGGGTTGGCACCA ACCTGGAAGATCCGGCGTCTCGTGATCTGGTTGTTTCT TACGTTAACACTAACGTTGGTCTGAAATTCCGTCAGCT GCTGTGGTTCCACATCTCTTGCCTGACCTTCGGTCGTG AAACCGTTCTGGAATACCTGGTTTCTTTTGGTGTTTGG ATTCGTACTCCGCCGGCTTACCGTCCGCCGAACGCAC CGATCCTGAGCACCCTGCCGGAAACCACTGTTGTGTA ATAA (SEQ ID NO: 15) |
| Original (M66S-L76M) | MDIDPYKEFGATVELLS FLPSDFFPSVRDLLDTA AALYRDALESPEHCSPH HTALRQAILCWGDL<u>S</u>TL ATWVGTN<u>M</u>EDPASRDL VVSYVNTNVGLKFRQLL WFHISCLTFGRETVLEY LVSFGVWIRTPPAYRPP NAPILSTLPETTVV (SEQ ID NO: 2) | ATGGATATCGACCCGTACAAAGAATTCGGCGCGACCG TTGAACTGCTGTCTTTCCTGCCGTCTGATTTCTTCCCG TCTGTTCGTGACCTGCTGGACACCGCGGCAGCACTGT ACCGTGACGCGCTGGAATCTCCGGAACATTGTTCTCC GCATCACACTGCGCTGCGTCAGGCGATTCTGTGCTGG GGCGACCTGa<u>gc</u>ACCCTGGCGACTTGGGTTGGCACCA AC<u>atg</u>GAAGATCCGGCGTCTCGTGATCTGGTTGTTTCTT ACGTTAACACTAACGTTGGTCTGAAATTCCGTCAGCTG CTGTGGTTCCACATCTCTTGCCTGACCTTCGGTCGTGA AACCGTTCTGGAATACCTGGTTTCTTTTGGTGTTTGGA TTCGTACTCCGCCGGCTTACCGTCCGCCGAACGCACC GATCCTGAGCACCCTGCCGGAAACCACTGTTGTGTAAT AA (SEQ ID NO: 16) |
| HBc(HP) | MDIDPYKEFGATVELLSFLPSDFFPSVRCLLDTAAALYRDALESPEHCSPHHTALRQA<u>VSCW REVTDFGDWVGNNMQDQAARDLVVNYVNANIGLKI</u>RQLLWFHISCLTFGRETVLEYLVSFGV WI<u>C</u>TPPAYRPPNAPILSTLPETTVV (SEQ ID NO: 3) | |

What is claimed is:

1. A hepatitis B core protein (HBc) polypeptide, comprising a hydrophobic cargo-loading domain at the carboxy terminus, wherein the cargo-loading domain is selected from EGFGEGFGEGF (SEQ ID NO:4); EGFGEGFGEGFC (SEQ ID NO:5); IGIGC (SEQ ID NO:6); and IGIGIC (SEQ ID NO:7).

2. The HBc polypeptide of claim 1, wherein the cargo-loading domain comprises one cysteine residue.

3. The HBc polypeptide of claim 1, further comprising a C-terminal poly-histidine tag before or after the cargo-loading domain.

4. The HBc polypeptide of claim 1, wherein the polypeptide further comprises at least one unnatural amino acid.

5. The HBc polypeptide of claim 4, wherein the unnatural amino acid provides a reactant group for Click chemistry reactions.

6. The HBc polypeptide of claim 5, wherein the unnatural amino acid is azidohomoalanine, homopropargylglycine, p-acetyl-L-phenylalanine or p-azido-L-phenylalanine.

7. The HBc polypeptide of claim 6, further comprising one or more additional moieties conjugated to the unnatural amino acid.

8. A VLP comprised of HBc polypeptides according to claim 1.

9. The VLP of claim 8, wherein the VLP comprises encapsulated cargo.

10. The VLP of claim 9, wherein the cargo is ssRNA, dsRNA, ssDNA, dsDNA, protein, or small molecule drug by loading mediated by hydrophobic interaction directly to the cargo or to a hydrophobic moiety attached to the cargo.

11. The VLP of claim 9, wherein the cargo is a chemotherapeutic drug.

12. The VLP of claim 9, wherein the cargo is modified to enhance retention or uptake.

13. The VLP of claim 12, wherein the cargo is modified by conjugation to cholesterol.

14. The VLP of claim 12, wherein the cargo is modified to add a single sulfhydryl group.

15. The HBc polypeptide of claim 1, wherein the cargo-loading domain comprises from one to three hydrophobic amino acids.

16. A method of assembling a cargo loaded VLP, the method comprising adding cargo to a solution comprising a polypeptide according to claim 1, and increasing ionic strength of the solution with a solution comprising at least 10% of an organic solvent.

17. The method of claim 16, wherein the organic solvent is DMSO.

* * * * *